US007339082B2

(12) United States Patent
Ishihara et al.

(10) Patent No.: US 7,339,082 B2
(45) Date of Patent: *Mar. 4, 2008

(54) ARYLBIS(PERFLUOROALKYLSULFONYL)METHANE AND METALLIC SALT THEREOF, AND METHODS FOR PRODUCING THE SAME

(75) Inventors: Kazuaki Ishihara, Konan (JP); Hisashi Yamamoto, Chicago, IL (US)

(73) Assignee: Japan Science and Technology Corporation, Kawaguchi-Shi, Saitama (JP)

( * ) Notice: Subject to any disclaimer, the term of this patent is extended or adjusted under 35 U.S.C. 154(b) by 467 days.

This patent is subject to a terminal disclaimer.

(21) Appl. No.: 10/996,216

(22) Filed: Nov. 22, 2004

(65) Prior Publication Data
US 2005/0070741 A1 Mar. 31, 2005

Related U.S. Application Data

(62) Division of application No. 10/450,349, filed as application No. PCT/JP01/10978 on Dec. 14, 2001, now Pat. No. 7,193,113.

(30) Foreign Application Priority Data

| Dec. 15, 2000 | (JP) | ............................. 2000-381537 |
| Dec. 15, 2000 | (JP) | ............................. 2000-381539 |
| Sep. 18, 2001 | (JP) | ............................. 2001-283216 |
| Sep. 18, 2001 | (JP) | ............................. 2001-283217 |

(51) Int. Cl.
*C07C 315/04* (2006.01)
(52) U.S. Cl. ......................................................... 568/35
(58) Field of Classification Search ..................... None
See application file for complete search history.

(56) References Cited

U.S. PATENT DOCUMENTS

| 4,049,861 | A | 9/1977 | Nozari ........................ 428/220 |
| 4,069,368 | A | 1/1978 | Deyak et al. |
| 4,115,295 | A | 9/1978 | Robins et al. |
| 4,337,107 | A | 6/1982 | Eshleman |
| 4,431,845 | A | 2/1984 | Young et al. |
| 4,830,847 | A | 5/1989 | Benedict et al. |
| 5,071,737 | A | 12/1991 | Kita et al. |
| 5,932,511 | A | 8/1999 | Harmer et al. |
| 2004/0030192 | A1 | 2/2004 | Ishihara et al. |
| 2004/0116617 | A1 | 6/2004 | Ishihara et al. |

FOREIGN PATENT DOCUMENTS

| EP | 0 386 930 A1 | 9/1990 |
| EP | 0 985 662 A2 | 3/2000 |
| EP | 1 375 532 A | 1/2004 |
| GB | 2 285 442 A | 7/1995 |
| JP | 3-254697 | 11/1991 |
| JP | 07 246338 A | 9/1995 |
| WO | WO 00/44495 A | 8/2000 |

OTHER PUBLICATIONS

Hendrickson et al, Journal of the American Chemical Society, Triflones (CF3SO2C), A Survey of Reactivity and Synthetic Utility, 1974, 96, pp. 2275-2276.*
Patent Abstracts of Japan, English abstract of JP 07 246338A, Sep. 26, 1995.
Patent Abstracts of Japan, English abstract of JP 03 254697, Nov. 1991.
Nagayama et al, "A Novel Polymer-Supported Scandium Catalyst Which Shows High Activity in Water," Angewandte Chemie International Edition, vol. 39, No. 3, Feb. 1, 2000, pp. 567-569.
Ishihara et al, "Polystyrene-bound Tetrafluorophenylbis(triflyl)methane As An Organic-Solvent-Swellable And Strong Bronsted Acid Catalyst," Angewandte Chemie International Edition, vol. 40, No. 21, Nov. 5, 2001, pp. 4077-4079.
Ishihara et al, "Polystyrene-bound Tetrafluorophenylbis(triflyl)methane As An Organic-Solvent-Swellable And Strong Bronsted Acid Catalyst," Angewandte Chemie, vol. 113, No. 21, Nov. 5, 2001, pp. 4201-4203.
Ishihara et al, "Scandium Trifluoromethanesulfonate as an extremely active lewis acid catalyst in acylation of alcohols with acid anhydrides and mixed anhydrides," Journal of Organic Chemistry, vol. 61, 1996, pp. 4560-4567.
Ishihara et al, "Pyrolysis of benzenediazonium bis(trifluoromethanesulfonyl)methide" Journal of Fluorine Chemistry, vol. 106, pp. 139-141, 2000.
Zhu, Shizheng, "Synthesis and Reactions of Phenyliodonium Bis(perfluoroalkanesulfonyl) Methides," Heteroatom Chemistry, 1994, vol. 5, No. 1, pp. 9-18.
Zhu, Shizheng, "A new synthetic route to aryl bis(perfluoroalkanesulfonyl)methanes; structures of tolyldiazonium bis(trifluoromethanesulfonyl)methide and 4-nitrophenyl-hydrazono bis(trifluoromethanesulfonyl)methane" J. Fluorine Chem., 1993, vol. 64, pp. 47-60.
Liston, David J. et al, "Observations on Silver Salt Metathesis Reactions with Very Weakly Coordinating Anions" J. Am. Chem. Soc., 1989, vol. 111, pp. 6643-6648.
English translation of the International Preliminary Examination Report (Form PCT/IB/409), and Notification of Transmittal (Form PCT/IB/338); mailed Oct. 2, 2003, from the International Bureau.

* cited by examiner

*Primary Examiner*—Paul A. Zucker
(74) *Attorney, Agent, or Firm*—Morgan & Finnegan, LLP

(57) ABSTRACT

The present invention provides a method for producing various types of arylbis(perfluoroalkylsulfonyl)methane having a bulky aryl group and an electron-accepting aryl group in which synthesis was conventionally considered to be difficult, at high efficiency; a novel arylbis(perfluoroalkylsulfonyl)methane that can be widely applied to asymmetric catalyst, various types of functional materials and the like; and a metallic salt thereof. In addition, excellent catalysts are also provided. An aryl halomethane is reacted with a sodium trifluoromethane sulfinate, the arylmethyl triflone produced thereby is reacted with a t-BuLi and the like, the lithium salt of the arylmethyl triflone obtained is reacted with a trifluoromethane sulfinic acid anhydride, and an arylbis (trifluoromethylsulfony)methane such as pentafluorophenylbis(triflyl)methane, {4-(pentafluorophenyl)-2,3,5,6-tetrafluorophenyl}bis(triflyl)methane and the like are obtained at a high yield.

11 Claims, No Drawings

ARYLBIS (PERFLUOROALKYLSULFONYL)METHANE AND METALLIC SALT THEREOF, AND METHODS FOR PRODUCING THE SAME

This application is a DIV of Ser. No. 10/450,349, filed Jun. 12, 2003, now U.S. Pat. No. 7,193,113, which is a 371 of PCT/JP01/10978 filed Dec. 14, 2001.

TECHNICAL FIELD

The present invention relates to a method for producing arylbis(perfluoroalkylsulfonyl)methane such as arylbis(triflyl)methane and the like, by using sodium trifluoromethane sulfinate and trifluoromethane sulfinic acid anhydride as an electrophilic reactant used as a triflyl source, and a novel arylbis(perfluoroalkylsulfonyl)methane such as pentafluorophenylbis(triflyl)methane, {4-(pentafluorophenyl)-2,3,5,6-tetrafluorophenyl}bis(triflyl)methane and the like obtained from said method.

Moreover, the present invention relates to a metallic salt of arylbis(perfluoroalkylsulfonyl)methane, that is, a metallic arylbis(perfluoroalkylsulfonyl)methide, a method for producing said compound, catalysts such as Lewis acid catalyst which comprises said compound as an active ingredient, and a method for synthesizing organic compounds by using said catalysts.

BACKGROUND ART

Trifluoromethane sulfonyl (—$SO_2CF_3$; triflyl, Tf) group is known as one of the strongest electron-accepting group, which has an action to increase the protonic acidity of its α position (J. Am. Chem. Soc. 96, 2275, 1974; Synthesis, 691, 1997; J. Fluorine Chem. 66, 301, 1994). For example, bis(triflyl)methane ($CH_2Tf_2$; $pK_a(H_2O)=-1$) (J. Am. Chem. Soc. 106, 1510, 1984) and phenylbis(triflyl)methane (Ph-$CHTf_2$; $pK_a(MeCN)=7.83$) (J. Org. Chem. 63, 7868, 1998) are strong acids that do not have the ability to oxidize. The inherent acidity $\Delta G_{acid}$ (in gas condition) estimated by Koppel et al. is as follows (J. Am. Chem. Soc. 116, 3047, 1994): $MeSO_3H$ (315.0)<$CH_2Tf_2$ (310.5)<$PhCHTf_2$ (310.3)<TfOH (299.5)<$NHTf_2$ (291.8)<$CHTf_3$ (289.0). These volatile crystalline solids are known to serve as a reactant when preparing a cationic organometallic dihydrido by protonating an organometallic hydrido (J. Am. Chem. Soc. 106, 1510, 1984; J. Chem. Soc., Chem. Commun. 1675, 1987; Inorg. Chem. 27, 1593, 1988; Inorg. Chem. 27, 2473, 1988; Organometallics 9, 1290, 1990). Based on these facts, it is expected that the steric and electronic effects of the aromatic group in the arylbis(triflyl)methane such as phenylbis(triflyl)methane and the like mentioned above, have a great effect on its Broensted acidity and the property of their organometallic complex.

Heretofore, two methods have been known as a method for synthesizingthe phenylbis(triflyl)methane mentioned above (J. Org. Chem. 38, 3358, 1973; Heteroatom Chem. 5, 9, 1994; J. Fluorine Chem. 64, 47, 1993; J. Fluorine Chem. 106, 139, 2000). One of the methods is a method wherein benzyl magnesium chloride is reacted with triflyl fluoride to synthesize phenylbis(triflyl)methane (40% yield) (J. Org. Chem. 38, 3358, 1973), and the other method is a method wherein light response between iodobenzene bis(triflylmethide) and benzene is conducted (61% yield) (Heteroatom Chem. 5, 9, 1994). The former requires a triflyl fluoride gas (bp=−21° C.) which is difficult to obtain, as a triflyl source, and the latter requires an excessive amount of benzene, a reactant, as a solvent. Moreover, in the case of the latter, arylbis(triflyl)methane is not formed when light response is conducted with allene, which has an electron-accepting group such as fluorobenzene.

Meanwhile, a method for synthesizing benzyl triflone has been reported by Hendrickson et al. (J. Am. Chem. Soc. 96, 2275, 1974; Synthesis, 691, 1997; J. Fluorine Chem. 66, 301, 1994). However, there was a problem that arylmethyl triflone could not be synthesized at a high yield when the aromatic group is an electron-accepting group and is inactivated (Synthesis, 691, 1997).

In addition, Lewis acid catalyst is known to be the most widely used catalyst in the aspect of organic synthesis. This Lewis acid catalyst associates with a specific functional group of an organic compound, forms a complex, and can be made to conduct a particular response only. The one that accepts an electron pair from which it reacts with is referred to as Lewis acid. Organic compounds generally have a functional group, and the functional group is usually a Lewis base, which attracts mutually with Lewis acid. The Lewis acid catalyst designed in this manner forms a complex with the functional group of the organic compound, and leads directly to the desired reaction. Due to this point, Lewis acid catalyst is also compared to an artificial enzyme. However, the reactivity and selectivity of the conventional Lewis acid catalyst was not so high compared to when enzyme was used, and was not sufficient. Therefore, a Lewis acid catalyst that has an excellent selectivity and reactivity, and further capable of reacting under warm condition has been required.

Heretofore, a Lewis acid catalyst comprised of a compound shown by a general formula $M[RfSO_2—N—SO_2Rf']_n$ or $M[RfSO_2—N—SO_2Rf']_n·mH_2O$ (wherein Rf and Rf' represent a perfluoroalkyl group having 1 to 8 carbon atoms, M represents an element selected from alkaline metal, alkaline earth metal, transition metal, rare earth, aluminum, gallium, iridium, thallium, silicon, germanium, tin, lead, arsenic, antimony, bismuth, selenium and tellurium, n represents an integer of the same number as the valence of the corresponding metal, and m represents a natural number from 0.5 to 20) (Japanese Laid Open Patent Application No. 07-246338), and a Lewis acid catalyst shown by the following formula,

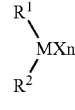

(Chemical formula 1)

[7]

[wherein X represents —N(Tf¹)Tf² [wherein Tf¹ represents —$SO_2Rf^1$, Tf² represents —$SO_2Rf^2$ (wherein each of Rf¹ and Rf² independently represents a fluorine atom or a perfluoroalkyl group)], R¹ represents a substituted or unsubstituted cyclopentadienyl group, —OR³ or —N(Tf³)R⁴, R² represents a substituted or unsubstituted cyclopentadienyl group, —OR⁵ or —N(Tf⁴)R⁶ [wherein Tf³ represents —$SO_2Rf^3$, Tf⁴ represents —$SO_2Rf^4$ (wherein each of Rf³ and Rf⁴ independently represents a fluorine atom or a perfluoroalkyl group), each of R³, R⁴, R⁵ and R⁶ independently represents a lower alkyl group, or, R³ and R⁵, R³ and R⁶, R⁴ and R⁵ or R⁴ and R⁶ form together a bivalent group], M represents an element selected from alkaline earth metal, rare earth element, transition metal, boron, aluminum, gallium, indium, thallium, silicon, germanium, tin, lead, arsenic, antimony, bismuth, selenium or tellurium, n represents an integer of valence −2 of the corresponding M, and has at least one of —N(Tf$^1$)Tf$^2$, —N(Tf$^3$)R$^4$ or —N(Tf$^4$)R$^6$] (Japanese Laid Open Patent Application No. 09-57110), have been known as Lewis acid catalysts.

Aside from the examples mentioned above, there have been disclosures of highly active acid catalysts, including a highly active Lewis acid catalyst that can be used under the coexistence of water, comprising a metallic halide shown by a general formula M$^+$(X$_1^-$)q (wherein M represents at least one metal selected from a group comprising elements from IIIA family to VB family of the periodic table, X$_1$ represents a halogen atom, and q represents an integer that is identical to the valence number of M) and a quaternary salt type anion exchange resin (Japanese Laid Open Patent Application No. 09-262479), and an acid catalyst comprising a metallic salt of tris(perfluoroalkylsulfonyl)methide shown by the following formula [(RfSO$_2$)$_3$C]$_n$M$_2$ (however, Rf represents a perfluoroalkyl group having one or more carbon atoms, M$_2$ represents an element selected from alkaline metal, alkaline earth metal, transition metal including rare earth, zinc, cadmium, aluminum, gallium, indium, thallium, silicon, germanium, tin, lead, arsenic, antimony, bismuth, selenium or tellurium. n represents an integer of the same number as the valence of M$_2$) (Japanese Laid Open Patent Application No. 2000-219692).

Heretofore, TfOH, Tf$_2$NH, Tf$_2$CH$_2$ and Tf$_3$CH have already been known as an organic acid having a triflyl group. However, chemical modification to these molecules is not easy and therefore, it is difficult to make the molecules have a novel function. Due to this reason, they were not considered to be an appropriate material when producing pharmaceuticals, agricultural chemicals, asymmetric catalysts, various types of functional materials and the like. Moreover, recently, the development of a catalyst capable of easily conducting asymmetric synthesis, which is called chiral technology or chiral industry in the field of medicine and agricultural chemical, is expected for the development and application of pharmaceuticals, agricultural chemicals, various types of functional materials and the like.

The object of the present invention is to provide: a method wherein an arylbis(perfluoroalkylsulfonyl)methane such as the various types of arylbis(triflyl)methane and the like having a bulky aryl group and an electron-accepting aryl group in which its synthesis was conventionally considered to be difficult, is produced easily and highly efficiently; a novel arylbis(perfluoroalkylsulfonyl)methane such as pentafluorophenylbis(triflyl)methane, {4-(pentafluorophenyl)-2,3,5,6-tetrafluorophenyl}bis(triflyl)methane and the like, which can be widely applied to asymmetric catalyst, various types of functional materials and the like; a method for producing a metallic salt of arylbis(perfluoroalkylsulfonyl)methane that has excellent selectivity and reactivity, can further react under warm condition, and introduce various types of aryl groups, that is, metallic arylbis(perfluoroalkylsulfonyl)methide, wherein said arylbis(perfluoroalkylsulfonyl)methane is used,; a metallic arylbis(perfluoroalkylsulfonyl)methide obtained by said method; catalysts such as Lewis acid catalyst and the like comprised of said compound; and a method for synthesizing organic compounds by using said catalysts.

DISCLOSURE OF THE INVENTION

The present inventors have found out that arylbis(trifluoromethylsulfonyl)methane can be produced at a high yield by the following steps: an easily obtainable aryl halomethane was used as a starting material; sodium trifluoromethane sulfinate (TfNa) was used as an electrophilic reactant as a triflyl source; heating under reflux was conducted with the use of propionitrile as a solvent under the presence of 10 mol % tetrabutyl ammonium iodide catalyst to conduct nucleophilic substitution; arylmethyl trifluoromethylsulfone was produced at a high yield; and 2.2 equivalent weight of tert-butyl lithium (t-BuLi) and 1.1 equivalent weight of trifluoromethane sulfinic acid anhydride (Tf$_2$O) were sequentially added to the arylmethyl trifluoromethylsulfone produced. Thus, the present invention had been completed.

Further, the present inventors conducted a keen study to elucidate the object mentioned above. In the same manner as the method described above, TfNa and Tf$_2$O were used to synthesize pentafluorophenylbis(triflyl)methane; the pentafluorophenylbis(triflyl)methane obtained was subjected to heating under reflux with scandium oxide (Sc$_2$O$_3$) in water to produce scandium (III) pentafluorophenylbis(triflyl); said compound was used as a Lewis acid catalyst for benzoylation reaction with menthol and benzoic acid anhydride, and Diels-Alder reaction of methacrolein with cyclopentadiene; and it was confirmed that said compound has a better catalyst activity than the existing Lewis acids. Thus, the present invention has been completed.

The present invention relates to an arylbis(perfluoroalkylsulfonyl)methane represented by the following general formula [1]

(Chemical formula 2)

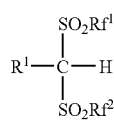

[1]

(wherein R$^1$ shows a substituted or unsubstituted aryl group (however, phenyl group is excluded), Rf$^1$ and Rf$^2$ are independent to each other and show a perfluoroalkyl group) (claim 1); the arylbis(perfluoroalkylsulfonyl)methane represented by the general formula [1] according to claim 1, wherein R$^1$ is a naphthyl group, a 2,4,6-trimethylphenyl group, a 4-(trifluoromethyl)phenyl group, a 3,5-bis(trifluoromethyl)phenyl group, a pentafluorophenyl group or a perfluorobiphenyl group (claim 2); the arylbis(perfluoroalkylsulfonyl)methane represented by the general formula [1] according to claim 1, wherein Rf$^1$ and Rf$^2$ are both a trifluoromethyl group (claim 3); a pentafluorophenylbis(trifluoromethylsulfonyl)methane represented by formula [2]

(Chemical formula 3)

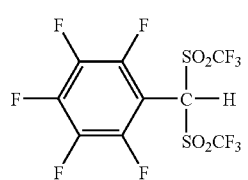

[2]

or a para position substituent thereof (claim 4); and a {4-(pentafluorophenyl)-2,3,5,6-tetrafluorophenyl}bis(triflyl)methane represented by formula [3]

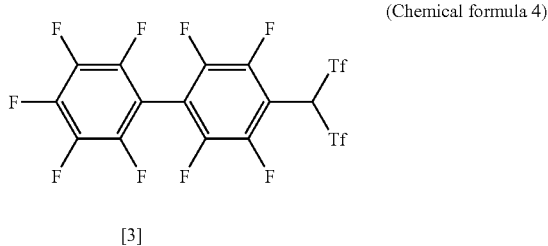

(Chemical formula 4)

[3]

or a 4' position substituent thereof (claim 5).

Further, the present invention relates to a method for producing an arylbis(perfluoroalkylsulfonyl)methane represented by general formula [4]

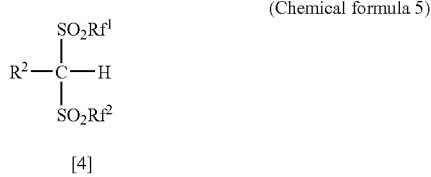

(Chemical formula 5)

[4]

(wherein $R^2$ shows a substituted or unsubstituted aryl group, $Rf^1$ and $Rf^2$ are independent to each other and show a perfluoroalkyl group), wherein an aryl halomethane is reacted with a perfluoroalkyl sulfinate, an arylmethylperfluoroalkylsulfone produced is reacted with a deprotonation agent comprised of an organic metal or a metallic salt, and a metallic salt of arylmethylperfluoroalkylsulfone obtained is reacted with a perfluoroalkyl sulfinic acid anhydride (claim 6); the method for producing the arylbis(perfluoroalkylsulfonyl)methane represented by the general formula [4] according to claim 6, wherein the aryl halomethane is reacted with the perfluoroalkyl sulfinate by heating under reflux using a solvent with or without the presence of a catalyst (claim 7); the method for producing the arylbis(perfluoroalkylsulfonyl)methane represented by the general formula [4] according to claim 7, wherein a tetrabutyl ammonium iodide is used as the catalyst (claim 8); the method for producing the arylbis(perfluoroalkylsulfonyl)methane represented by the general formula [4] according to claim 7, wherein a propionitrile is used as the solvent (claim 9); the method for producing the arylbis(perfluoroalkylsulfonyl)methane represented by the general formula [4] according to claim 6, wherein a deprotonation agent comprised of an organic metal or a metallic salt having an equivalent weight of 1.7 to 2.4 is reacted to the arylmethylperfluoroalkylsulfone (claim 10); the method for producing the arylbis(perfluoroalkylsulfonyl)methane represented by the general formula [4] according to claim 6, wherein the aryl halomethane is a benzyl bromide, a 2-bromomethylnaphthalene, a 1-chloromethylnaphthalene, a 2,4,6-trimethylphenylmethylchloride, a 4-(trifluoromethyl)phenylmethylbromide, a 3,5-bis(trifluoromethyl)phenylmethylbromide, a pentafluorophenylmethylbromide or a 4-(bromomethyl)perfluorobiphenyl (claim 11); the method for producing the arylbis(perfluoroalkylsulfonyl)methane represented by the general formula [4] according to claim 6, wherein the perfluoroalkyl sulfinate is an alkaline metallic salt of trifluoromethane sulfinic acid (claim 12); the method for producing the arylbis(perfluoroalkylsulfonyl)methane represented by the general formula [4] according to claim 6, wherein the metallic salt of arylmethylperfluoroalkylsulfone is a lithium salt or a magnesium salt of arylmethylperfluoroalkylsulfone (claim 13); the method for producing the arylbis(perfluoroalkylsulfonyl)methane represented by the general formula [4] according to claim 6, wherein the arylbis(perfluoroalkylsulfonyl)methane represented by the general formula [4] is an arylbis(trifluoromethylsulfonyl)methane represented by general formula [5]

(Chemical formula 6)

[5]

(wherein $R^2$ shows a substituted or unsubstituted aryl group) (claim 14); the method for producing the arylbis(perfluoroalkylsulfonyl)methane represented by the general formula [4] according to claim 14, wherein the arylbis(trifluoromethylsulfonyl)methane represented by the general formula [5] is a pentafluorophenylbis(trifluoromethylsulfonyl)methane represented by formula [2]

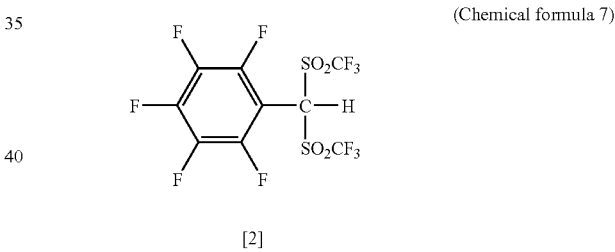

(Chemical formula 7)

[2]

(claim 15); and the method for producing the arylbis(perfluoroalkylsulfonyl)methane represented by the general formula [4] according to claim 14, wherein the arylbis(trifluoromethylsulfonyl)methane represented by the general formula [5] is a {4-(pentafluorophenyl)-2,3,5,6-tetrafluorophenyl}bis(triflyl)methane represented by formula [3]

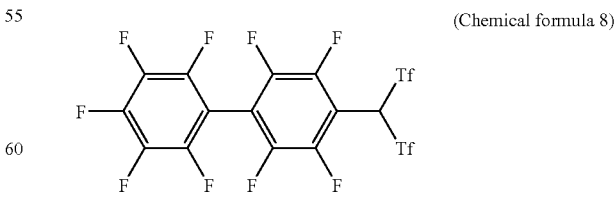

(Chemical formula 8)

[3]

(claim 16).

The present invention relates to a metallic salt of arylbis(perfluoroalkylsulfonyl)methane represented by general formula [6]

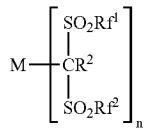

(Chemical formula 9)

[6]

(wherein $R^2$ shows a substituted or unsubstituted aryl group (however, phenyl group is excluded), $Rf^1$ and $Rf^2$ are independent to each other and show a perfluoroalkyl group, M shows any one of the elements selected from alkaline metallic element, alkaline earth metallic element, transition metallic element, boron, silicon, aluminum, tin, zinc or bismuth, n shows a numeric value equal to the valence of M element) (claim 17); the metallic salt of arylbis(perfluoroalkylsulfonyl)methane according to claim 17, wherein the transition metallic element is any one of the metallic elements selected from scandium, yttrium, lanthanoid, copper, silver, titanium, zirconium or hafnium (claim 18); the metallic salt of arylbis(perfluoroalkylsulfonyl)methane according to claim 17, wherein $Rf^1$ and $Rf^2$ are both a trifluoromethyl group (claim 19); the metallic salt of arylbis(perfluoroalkylsulfonyl)methane according to claim 17, wherein $R^2$ is a phenyl group, a naphthyl group, a 2,4,6-trimethylphenyl group, a 4-(trifluoromethyl)phenyl group, a 3,5-bis(trifluoromethyl)phenyl group, a pentafluorophenyl group or a perfluorobiphenyl group (claim 20); the metallic salt of arylbis(perfluoroalkylsulfonyl)methane according to claim 17, wherein the metallic salt of arylbis(perfluoroalkylsulfonyl)methane is a metallic salt of phenylbis(triflyl)methane, a metallic salt of 2-naphthylbis(triflyl)methane, a metallic salt of 1-naphthylbis(triflyl)methane, a metallic salt of 2,4,6-trimethylphenylbis(triflyl)methane, a metallic salt of 4-(trifluoromethyl)phenylbis(triflyl)methane, a metallic salt of 3,5-bis(trifluoromethyl)phenylbis(triflyl)methane, a metallic salt of pentafluorophenylbis(triflyl)methane or a metallic salt of {4-(pentafluorophenyl)-2,3,5,6-tetrafluorophenyl}bis(triflyl)methane (claim 21); the metallic salt of arylbis(perfluoroalkylsulfonyl)methane according to claim 21, wherein the metallic salt of pentafluorophenylbis(triflyl)methane is a scandium (III) pentafluorophenylbis(triflyl)methide or a lithium pentafluorophenylbis(triflyl)methide (claim 22); and the metallic salt of arylbis(perfluoroalkylsulfonyl)methane according to claim 21, wherein the metallic salt of {4-(pentafluorophenyl)-2,3,5,6-tetrafluorophenyl}bis(triflyl)methane is a scandium (III) {4-(pentafluorophenyl)-2,3,5,6-tetrafluorophenyl}bis(triflyl)methide or a lithium {4-(pentafluorophenyl)-2,3,5,6-tetrafluorophenyl}bis(triflyl)methide (claim 23).

Further, the present invention relates to a method for producing a metallic salt of arylbis(perfluoroalkylsulfonyl)methane, wherein the method is a method for producing a metallic salt of arylbis(perfluoroalkylsulfonyl)methane represented by general formula [6]

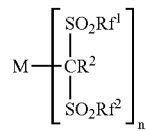

(Chemical formula 10)

[6]

(wherein $R^2$ shows a substituted or unsubstituted aryl group, $Rf^1$ and $Rf^2$ are independent to each other and show a perfluoroalkyl group, M shows any one of the elements selected from alkaline metallic element, alkaline earth metallic element, transition metallic element, boron, silicon, aluminum, tin, zinc or bismuth, n shows a numeric value equal to the valence of M element) wherein an arylbis(perfluoroalkylsulfonyl)methane represented by general formula [4]

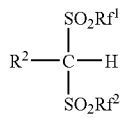

(Chemical formula 11)

[4]

(wherein $R^2$ shows a substituted or unsubstituted aryl group, $Rf^1$ and $Rf^2$ are independent to each other and show a perfluoroalkyl group) is neutralized with a hydroxide of a metal (claim 24); the method for producing the metallic salt of arylbis(perfluoroalkylsulfonyl)methane according to claim 24, wherein the hydroxide of the metal is a hydroxide of a metal selected from alkaline metal or alkaline earth metal (claim 25); the method for producing the metallic salt of arylbis(perfluoroalkylsulfonyl)methane according to claim 24, wherein the arylbis(perfluoroalkylsulfonyl)methane represented by the general formula [4] is used, which is obtained by reacting an aryl halomethane with a perfluoroalkyl sulfonate, followed by reacting an arylmethylperfluoroalkylsulfone produced with a deprotonation agent comprised of an organic metal or an metallic salt, and a metallic salt of arylmethylperfluoroalkylsulfone obtained is reacted with a perfluoroalkyl sulfinic acid anhydride (claim 26); the method for producing the metallic salt of arylbis(perfluoroalkylsulfonyl)methane according to claim 26, wherein the aryl halomethane is reacted with the perfluoroalkyl sulfonate by heating under reflux using a solvent with or without the presence of a catalyst (claim 27); the method for producing the metallic salt of arylbis(perfluoroalkylsulfonyl)methane according to claim 27, wherein a tetrabutyl ammonium iodide is used as the catalyst (claim 28); the method for producing the metallic salt of arylbis(perfluoroalkylsulfonyl)methane according to claim 27, wherein a propionitrile is used as the solvent (claim 29); the method for producing the metallic salt of arylbis(perfluoroalkylsulfonyl)methane according to claim 26, wherein the perfluoroalkyl sulfinate is an alkaline metallic salt of trifluoromethane sulfinic acid (claim 30); the method for producing the metallic salt of arylbis(perfluoroalkylsulfonyl)methane according to claim 26, wherein the metallic salt of arylmethylperfluoroalkylsulfone is a lithium salt or a magnesium salt of arylmethylperfluoroalkylsulfone (claim 31); a method for producing a metallic salt of arylbis(perfluoroalkylsulfonyl)methane, wherein the method is a method for producing a metallic salt of arylbis(perfluoroalkylsulfonyl)methane represented by general formula [6],

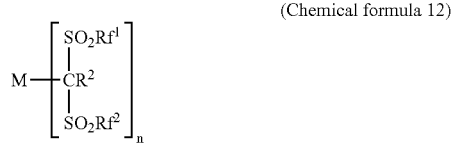

(Chemical formula 12)

[6]

(wherein R² shows a substituted or unsubstituted aryl group, Rf¹ and Rf² are independent to each other and show a perfluoroalkyl group, M shows any one of the elements selected from alkaline metallic element, alkaline earth metallic element, transition metallic element, boron, silicon, aluminum, tin, zinc or bismuth, n shows a numeric value equal to the valence of M element) wherein an arylbis(perfluoroalkylsulfonyl)methane represented by general formula [4]

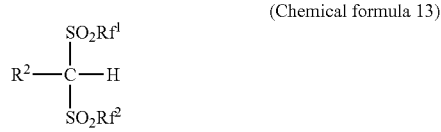

(Chemical formula 13)

[4]

(wherein R² shows a substituted or unsubstituted aryl group, Rf¹ and Rf² are independent to each other and show a perfluoroalkyl group) is reacted with a salt or an oxide of transition metal by heating under reflux (claim 32); the method for producing the metallic salt of arylbis(perfluoroalkylsulfonyl)methane according to claim 32, wherein the salt or the oxide of transition metal is a lanthanoid metallic salt or a scandium oxide (claim 33); the method for producing the metallic salt of arylbis(perfluoroalkylsulfonyl)methane according to claim 32, wherein the arylbis(perfluoroalkylsulfonyl)methane represented by the general formula [4] is used, which is obtained by reacting an aryl halomethane with a perfluoroalkyl sulfonate, followed by reacting an arylmethylperfluoroalkylsulfone produced with a deprotonation agent comprised of an organic metal or a metallic salt, and ametallic salt of arylmethylperfluoroalkylsulfone obtained is reacted with a perfluoroalkyl sulfonic acid anhydride (claim 34); the method for producing the metallic salt of arylbis(perfluoroalkylsulfonyl)methane according to claim 34, wherein the aryl halomethane is reacted with the perfluoroalkyl sulfonate by heating under reflux using a solvent with or without the presence of a catalyst (claim 35); the method for producing the metallic salt of arylbis(perfluoroalkylsulfonyl)methane according to claim 35, wherein a tetrabutyl ammonium iodide is used as the catalyst (claim 36); the method for producing the metallic salt of arylbis(perfluoroalkylsulfonyl)methane according to claim 35, wherein a propionitrile is used as the solvent (claim 37); the method for producing the metallic salt of arylbis(perfluoroalkylsulfonyl)methane according to claim 34, wherein the perfluoroalkyl sulfonate is an alkaline metallic salt of trifluoromethane sulfinic acid (claim 38); and the method for producing the metallic salt of arylbis(perfluoroalkylsulfonyl)methane according to claim 34, wherein the metallic salt of arylmethylperfluoroalkylsulfone is a lithium salt or a magnesium salt of arylmethylperfluoroalkylsulfone (claim 39).

The present invention also relates to a method for producing a metallic salt of arylbis(perfluoroalkylsulfonyl) methane, wherein the method is a method for producing a metallic salt of arylbis(perfluoroalkylsulfonyl)methane represented by general formula [6]

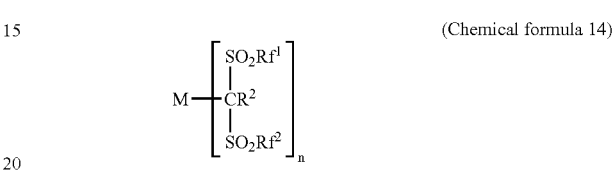

(Chemical formula 14)

[6]

(wherein R² shows a substituted or unsubstituted aryl group, Rf¹ and Rf² are independent to each other and show a perfluoroalkyl group, M shows any one of the elements selected from alkaline metallic element, alkaline earth metallic element, transition metallic element, boron, silicon, aluminum, tin, zinc or bismuth, n shows a numeric value equal to the valence of M element) wherein a metallic salt of arylbis(perfluoroalkylsulfonyl)methane represented general formula [4]

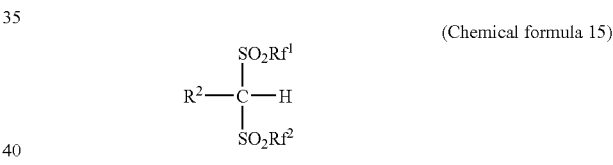

(Chemical formula 15)

[4]

(wherein R² shows a substituted or unsubstituted aryl group. Rf¹ and Rf² are independent to each other and show a perfluoroalkyl group) is reacted with a halide of a metal having different metal species (claim 40); the method for producing the metallic salt of arylbis(perfluoroalkylsulfonyl)methane according to claim 40, wherein the metallic salt of arylbis(perfluoroalkylsulfonyl)methane represented by the general formula [6] is a silver salt of arylbis(perfluoroalkylsulfonyl)methane (claim 41); the method for producing the metallic salt of arylbis(perfluoroalkylsulfonyl)methane according to claim 40, wherein the arylbis(perfluoroalkylsulfonyl)methane represented by the general formula [4] is used, which is obtained by reacting an aryl halomethane with a perfluoroalkyl sulfinate, followed by reacting an arylmethylperfluoroalkylsulfone produced with a deprotonation agent comprised of an organic metal or a metallic salt, and a metallic salt of arylmethylperfluoroalkylsulfone obtained is reacted with a perfluoroalkyl sulfinic acid anhydride (claim 42); the method for producing the metallic salt of arylbis(perfluoroalkylsulfonyl)methane according to claim 42, wherein the aryl halomethane is reacted with the perfluoroalkyl sulfonate by heating under reflux using a solvent with or without the presence of a catalyst (claim 43);

the method for producing the metallic salt of arylbis(perfluoroalkylsulfonyl)methane according to claim 43, wherein a tetrabutyl ammonium iodide is used as the catalyst (claim 44); the method for producing the metallic salt of arylbis (perfluoroalkylsulfonyl)methane according to claim 43, wherein a propionitrile is used as the solvent (claim 45); the method for producing the metallic salt of arylbis(perfluoroalkylsulfonyl)methane according to claim 42, wherein the perfluoroalkyl sulfinate is an alkaline metallic salt of trifluoromethane sulfinic acid (claim 46); and the method for producing the metallic salt of arylbis(perfluoroalkylsulfonyl)methane according to claim 42, wherein the metallic salt of arylmethylperfluoroalkylsulfone is a lithium salt or a magnesium salt of arylmethylperfluoroalkylsulfone (claim 47).

Further, the present invention relates to a method for producing a metallic salt of arylbis(perfluoroalkylsulfonyl)methane, wherein the method is a method for producing a metallic salt of arylbis(perfluoroalkylsulfonyl)methane represented by general formula [6]

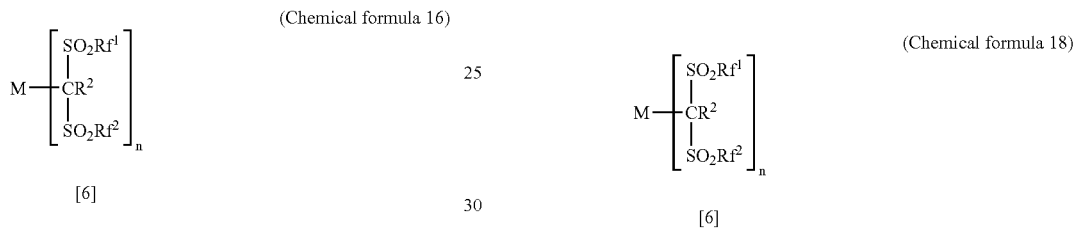

(Chemical formula 16)

[6]

(wherein $R^2$ shows a substituted or unsubstituted aryl group (however, phenyl group is excluded), $Rf^1$ and $Rf^2$ are independent to each other and show a perfluoroalkyl group, M shows any one of the elements selected from alkaline metallic element, alkaline earth metallic element, transition metallic element, boron, silicon, aluminum, tin, zinc or bismuth, n shows a numeric value equal to the valence of M element) wherein an arylbis(perfluoroalkylsulfonyl)methane represented by general formula [4]

(Chemical formula 17)

$$R^2\!-\!\underset{\underset{SO_2Rf^2}{|}}{\overset{\overset{SO_2Rf^1}{|}}{C}}\!-\!H$$

[4]

(wherein $R^2$ shows a substituted or unsubstituted aryl group, $Rf^1$ and $Rf^2$ are independent to each other and show a perfluoroalkyl group) is reacted with a silver carbonate under shade (claim 48); the method for producing the metallic salt of arylbis(perfluoroalkylsulfonyl)methane according to claim 48, wherein the arylbis(perfluoroalkylsulfonyl)methane represented by the general formula [4] is used, which is obtained by reacting an aryl halomethane with a perfluoroalkyl sulfonate, followed by reacting an arylmethylperfluoroalkylsulfone produced with a deprotonation agent comprised of an organic metal or a metallic salt, and a metallic salt of arylmethylperfluoroalkylsulfone obtained is reacted with a perfluoroalkyl sulfinic acid anhydride (claim 49); the method for producing the metallic salt of arylbis(perfluoroalkylsulfonyl)methane according to claim 49, wherein the aryl halomethane is reacted with the perfluoroalkyl sulfinate by heating under reflux using a solvent with or without the presence of a catalyst (claim 50); the method for producing the metallic salt of arylbis(perfluoroalkylsulfonyl)methane according to claim 50, wherein a tetrabutyl ammonium iodide is used as the catalyst (claim 51); the method for producing the metallic salt of arylbis (perfluoroalkylsulfonyl)methane according to claim 50, wherein a propionitrile is used as the solvent (claim 52); the method for producing the metallic salt of arylbis(perfluoroalkylsulfonyl)methane according to claim 49, wherein the perfluoroalkyl sulfinate is an alkaline metallic salt of trifluoromethane sulfinic acid (claim 53); and the method for producing the metallic salt of arylbis(perfluoroalkylsulfonyl)methane according to claim 49, wherein the metallic salt of arylmethylperfluoroalkylsulfone is a lithium salt or a magnesium salt of arylmethylperfluoroalkylsulfone (claim 54).

Moreover, the present invention relates to a catalyst having a metallic salt of arylbis(perfluoroalkylsulfonyl)methane represented by general formula [6]

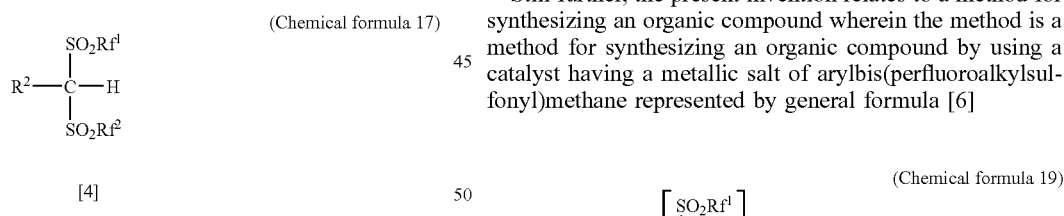

(Chemical formula 18)

[6]

(wherein $R^2$ shows a substituted or unsubstituted aryl group, $Rf^1$ and $Rf^2$ are independent to each other and show a perfluoroalkyl group, M shows any one of the elements selected from alkaline metallic element, alkaline earth metallic element, transition metallic element, boron, silicon, aluminum, tin, zinc or bismuth, n shows a numeric value equal to the valence of M element) as an active ingredient (claim 55); and the catalyst according to claim 55, wherein the catalyst is a Lewis acid catalyst (claim 56).

Still further, the present invention relates to a method for synthesizing an organic compound wherein the method is a method for synthesizing an organic compound by using a catalyst having a metallic salt of arylbis(perfluoroalkylsulfonyl)methane represented by general formula [6]

(Chemical formula 19)

$$M\!-\!\!\left[\!\!\begin{array}{c}SO_2Rf^1\\|\\CR^2\\|\\SO_2Rf^2\end{array}\!\!\right]_n$$

[6]

(wherein $R^2$ shows a substituted or unsubstituted aryl group, $Rf^1$ and $Rf^2$ are independent to each other and show a perfluoroalkyl group, M shows any one of the elements selected from alkaline metallic element, alkaline earth metallic element, transition metallic element, boron, silicon, aluminum, tin, zinc or bismuth, n shows a numeric value equal to the valence of M element) as an active ingredient, and catalytic reaction is conducted under the presence of said catalyst in a solvent (claim 57); and the method for synthesizing an organic compound according to claim 57, wherein the catalytic reaction is a benzoylation reaction, a Diels-Alder reaction, an Algol-type reaction, a Friedel-Crafts reaction, a Mannich reaction, a glycosilation reaction, an esterification reaction, an ene reaction, a cationic polymerization reaction or an allylation reaction (claim 58).

BEST MODE OF CARRYING OUT THE INVENTION

In the arylbis(perfluoroalkylsulfonyl)methane represented by the general formula [1] (wherein $R^1$ shows a substituted or unsubstituted aryl group (however, phenyl group is excluded), $Rf^1$ and $Rf^2$ are independent to each other and show a perfluoroalkyl group) of the present invention, examples of $R^1$ include an aryl group having a substituent such as a phenyl group, a naphthyl group, a biphenyl group and the like having a substituent, and an unsubstituted aryl group excluding phenyl group such as an α-naphthyl group, a β-naphthyl group, a biphenyl group and the like. Examples of the substituent for this case include a C1-C4 alkyl group such as methyl group and the like, a halogenated C1-C4 alkyl group such as trifluoromethyl group and the like, a halogen atom such as fluorine and the like, an alkoxy group, a sulfonyl group, an amino group and the like. Specific examples of said $R^1$ include a naphthyl group, a 2,4,6-trimethylphenyl group, a 4-(trifluoromethyl)phenyl group, a 3,5-bis(trifluoromethyl)phenyl group, a pentafluorophenyl group, a p-tolyl group, an m-tolyl group, a mesityl group, a xylyl group, a biphenyl group, a perfluorobiphenyl group, a p-chlorophenyl group, an o-chlorophenyl group and the like.

There is no particular limitation to the method for producing arylbis(perfluoroalkylsulfonyl) methane represented by the general formula [4] (wherein $R^2$ shows a substituted or unsubstituted aryl group, $Rf^1$ and $Rf^2$ are independent to each other and show a perfluoroalkyl group) of the present invention, as long as it is a method wherein an aryl halomethane is reacted with a perfluoroalkyl sulfonate, the arylmethylperfluoroalkylsulfone produced is reacted with a deprotonation agent comprised of an organic metal or a metallic salt, and the metallic salt of arylmethylperfluoroalkylsulfone obtained is reacted with an anhydrous perfluoroalkyl sulfonic acid. Moreover, the method for producing an arylbis(perfluoroalkylsulfonyl)methane obtained by further reacting the arylbis(perfluoroalkylsulfonyl)methane obtained by the method mentioned above with alkyl anion such as alkyl lithium, alkoxy anion such as alkoxy lithium and the like, is also included in the method of the present invention. Examples of $R^2$ in the formula [4] mentioned above include an aryl group such as a substituted or unsubstituted phenyl group, naphthyl group, biphenyl group and the like. Examples of the substituent for this case include a C1-C4 alkyl group such as methyl group and the like, a halogenated C1-C4 alkyl group such as trifluoromethyl group and the like, a halogen atom such as fluorine and the like, an alkoxy group, a sulfonyl group, an amino group and the like. Specific examples of said $R^2$ include a phenyl group, a naphthyl group, a 2,4,6-trimethylphenyl group, a 4-(trifluoromethyl)phenyl group, a 3,5-bis(trifluoromethyl) phenyl group, a pentafluorophenyl group, a p-tolyl group, a m-tolyl group, a mesityl group, a xylyl group, a biphenyl group, a perfluorobiphenyl group, a p-chlorophenyl group, an o-chlorophenyl group and the like.

The $Rf^1$ and $Rf^2$ in the general formulae [1] and [4] mentioned above show a perfluoroalkyl group that may be the same or different from each other, preferably a C1-C8 perfluoroalkyl group. Specific examples of $—SO_2Rf^1$ and $—SO_2Rf^2$ containing these $Rf^1$ and $Rf^2$ include a trifluoromethylsulfonyl group, a perfluoroethylsulfonyl group, a perfluoropropylsulfonyl group, a perfluoroisopropylsulfonyl group, a perfluorobutylsulfonyl group, a perfluoroisobutylsulfonyl group, a perfluoropentylsulfonyl group, a perfluoroisopentylsulfonyl group, a perfluoroneopentylsulfonyl group and the like.

Specific examples of the arylbis(perfluoroalkylsulfonyl)methane represented by the general formula [1] of the present invention are, for example, a 2-naphthylbis(triflyl)methane, a 1-naphthylbis(triflyl)methane, a 2,4,6-trimethylphenylbis(triflyl)methane, a 4-(trifluoromethyl)phenylbis(triflyl)methane, a 3,5-bis(trifluoromethyl)phenylbis(triflyl)methane, the pentafluorophenylbis(triflyl)methane represented by the formula [2], the {4-(pentafluorophenyl)-2,3,5,6-tetrafluorophenyl}bis(triflyl)methane represented by the formula [3] and the like. However, the examples are not limited to these. Further, examples of the compound of the present invention include: a para position substituent of the pentafluorophenylbis(triflyl)methane represented by the formula [2] mentioned above, for example, a para position alkyl substituent such as a p-phenyl-2,3,5,6-tetrafluorophenyl-bis(triflyl) and the like, a para position alkoxy substituent such as p-hexanoxy-2,3,5,6-tetrafluorophenyl-bis(triflyl) and the like; a 4' position substituent of the {4-(pentafluorophenyl)-2,3,5,6-tetrafluorophenyl}bis(triflyl)methane represented by the formula [3], for example, a 4' position alkyl substituent such as a [4-(4-phenyl-2,3,5,6-tetrafluorophenyl)-2,3,5,6-tetrafluorophenyl]bis(triflyl) and the like, a 4' position alkoxy substituent such as a [4-(4-hexanoxy-2,3,5,6-tetrafluorophenyl)-2,3,5,6-tetrafluorophenyl]bis(triflyl) methane and the like, etc.

A specific example of the arylbis(perfluoroalkylsulfonyl)methane represented by the general formula [4] in the method for producing the arylbis(perfluoroalkylsulfonyl)methane represented by the general formula [4] of the present invention is the arylbis(trifluoromethylsulfonyl)methane represented by the general formula [5] (wherein $R^2$ shows the aforementioned aryl group), which includes, for example, a phenylbis (triflyl)methane, a 2-naphthylbis(triflyl)methane, a 1-naphthylbis(triflyl)methane, a 2,4,6-trimethylphenylbis(triflyl)methane, a 4-(trifluoromethyl)phenylbis(triflyl)methane, a 3,5-bis(trifluoromethyl)phenylbis (triflyl)methane, the pentafluorophenylbis(triflyl)methane represented by the formula [2], the {4-(pentafluorophenyl)-2,3,5,6-tetrafluorophenyl}bis(triflyl)methane represented by the formula [3], and the like. However, the examples are not limited to these.

There is no particular limitation to the aryl halomethane used in the method for producing the arylbis(perfluoroalkylsulfonyl)methane represented by the general formula [4] of the present invention, as long as it is a methane substituted by a substituted or unsubstituted aryl group and a halogen atom. Specific examples include a benzyl bromide, a 2-bromomethylnaphthalene, a 1-chloromethylnaphthalene, a 2,4,6-trimethylphenylmethylchloride, a 4-(trifluoromethyl)phenylmethylbromide, a 3,5-bis(trifluoromethyl) phenylmethylbromide, a pentafluorophenylmethylbromide, a 4-(bromomethyl)perfluorobiphenyl(perfluorobiphenylmethylbromide) and the like.

A preferable example of the perfluoroalkyl sulfinate used in the method for producing the arylbis(perfluoroalkylsulfonyl)methane represented by the general formula [4] of the present invention is a metallic salt of a C1-C8 perfluoroalkyl sulfinic acid including, for example, a trifluoromethyl sulfonic acid, a perfluoroethyl sulfinic acid, a perfluoro propyl sulfinic acid, a perfluoroisopropyl sulfinic acid, a perfluorobutyl sulfinic acid, a perfluoroisobutyl sulfinic acid, a perfluoropentyl sulfinic acid, a perfluoroisopentyl sulfinic acid, a perfluoroneopentyl sulfinic acid and the like. An alkaline metallic salt and an alkaline earth metallic salt can be exemplified as the metallic salt, however, the alkaline metallic salt such as sodium and the like is preferable.

It is preferable for the nucleophilic substitution reaction of the aryl halomethane and the perfluoroalkyl sulfinate in the method for producing the arylbis(perfluoroalkylsulfonyl) methane represented by the general formula [4] of the present invention to be conducted in a condition wherein an arylmethylperfluoroalkylsulfone can be synthesized at a high efficiency, for example, by heating under reflux using a solvent with or without the presence of a catalyst. It is preferable for the molarity of the aryl halomethane in the reaction system mentioned above to be 0.2 to 0.4 M, and for the perfluoroalkyl sulfinate such as sodium trifluoromethane sulfinate to be used 1.0 to 1.5 equivalent weight, especially about 1.3 equivalent weight, to the aryl halomethane. In addition, when a catalyst is used, the use of a catalyst comprising an iodide such as tetrabutyl ammonium iodide, potassium iodide and the like is preferable. The amount of these catalysts to be used is, for example, 2 to 20 mol %, preferably 5 to 10 mol % to the aryl halomethane. Further, acetonitrile, propionitrile, nitromethane, nitropropane and the like can be given as examples of the solvent, however, it is preferable to use propionitrile in view of the applicability of the polarity and boiling point.

The synthesis reaction mentioned above is preferable to be conducted by heating under reflux in a dry inert gas atmosphere, such as in an argon or nitrogen atmosphere. It is preferable for the reaction to be conducted by heating under reflux at 80 to 150° C., preferably 100° C. to 120° C. for 12 to 48 hours. Examples of the methods for purifying the arylmethyl triflone obtained by these synthesis reactions are, for example, a method wherein the reactant solution obtained by reacting under the condition mentioned above is filtrated to remove salt, followed by a silica gel column chromatography using hexane and ethyl acetate (EtOAc) as a developing solvent, and a recrystallization operation using hexane and toluene, or the like.

Next, the arylbis(perfluoroalkylsulfonyl)methane represented by the general formula [4] can be produced by the reaction of an arylmethylperfluoroalkylsulfone produced by the nucleophilic substitution reaction of aryl halomethane and perfluoroalkyl sulfonate with a deprotonation agent comprising an organic metal or a metallic salt, followed by the reaction of the metallic salt of arylmethylperfluoroalkylsulfone obtained with a perfluoroalkyl sulfinic acid anhydride. However, there is no particular limitation to the deprotonation agent mentioned above, as long as it is an organic metal or a metallic salt having a deprotonating action. An alkaline metallic salt and alkaline earth metallic salt of lower alkyl, more specifically, t-BuLi and t-BuMgCl can preferably be exemplified. Further, a preferable example of the perfluoroalkyl sulfinic acid anhydride mentioned above is a C1-C8 perfluoroalkyl sulfinic acid anhydride including a trifluoromethane sulfinic acid anhydride ($Tf_2O$), a perfluoroethane sulfinic acid anhydride, a perfluoropropane sulfonic acid anhydride, a perfluoroisopropane sulfonic acid anhydride, a perfluorobutane sulfonic acid anhydride, a perfluoroisobutane sulfinic acid anhydride, a perfluoropentane sulfinic acid anhydride, a perfluoroisopentane sulfinic acid anhydride, a perfluoroneopentane sulfinic acid anhydride and the like. Among these, $Tf_2O$ is especially preferable.

There is no particular limitation to the method wherein the arylmethylperfluoroalkylsulfone mentioned above is reacted with a deprotonation agent such as alkyl lithium, alkyl magnesium chloride and the like and a perfluoroalkyl sulfinic acid anhydride such as $Tf_2O$ and the like, as long as it is a method which can produce arylbis(perfluoroalkylsulfonyl)methane such as arylbis(trifluoromethylsulfonyl)methane and the like at a high yield. Specific examples include, for example: a method wherein an arylmethylperfluoroalkylsulfone such as arylmethyl triflone and the like is dissolved in a solvent such as a diethylether and the like, alkyl lithium is added at −78° C., the solvent is reacted for 5 to 10 minutes, then $Tf_2O$ is added after the reaction to react for 1 to 2 hours at room temperature; and a method wherein alkyl magnesium chloride is added at −78° C. to react for 30 minutes, then reacted at 0° C. for 30 minutes, and $Tf_2O$ is added at −78° C. after the reaction to react for 1 to 2 hours at room temperature, and the like. However, it is preferable to repeat said operation multiple times, in view of the increase in yield.

Further, in order to obtain an arylbis(perfluoroalkylsulfonyl)methane such as arylbis(trifluoromethylsulfonyl)methane at a high yield, it is preferable to react 1.7 to 2.4 equivalent weight of an organic metal such as alkyl lithium and the like or 1.0 to 1.2 equivalent weight of a perfluoroalkyl sulfinic acid anhydride such as $Tf_2O$ and the like with the arylmethylperfluoroalkylsulfone such as arylmethyl triflone and the like. For example, in the case where t-BuLi (1.2 equivalent weight) is used for a benzyl triflone, since phenylbis(triflyl)methane is a much more stronger acid compared to the benzyl triflone, the phenylbis(triflyl)methane produced is immediately deprotonated by the lithium salt of the benzyl triflone, the phenylbis(triflyl)methane becomes a lithium salt, the lithium salt of the phenylbis(triflyl)methane obtained is converted to a phenyltris(triflyl)methane by the reaction with $Tf_2O$, the molar ratio of the benzyl triflone and the phenyltris(triflyl)methane becomes approximately 1:1, and only a little amount of the phenylbis(triflyl)methane is synthesized. However, in the case where 2.2 equivalent weight of t-BuLi is used for the benzyl triflone, the phenylbis(triflyl)methane produced is deprotonated by t-BuLi, and the benzyl triflone is quantitatively converted to a lithium salt of phenylbis(triflyl)methane.

However, in the case where a pentafluorophenylbis(triflyl)methane is produced by using a pentafluoromethylbromide, a pentafluorophenylbis(triflyl)methane and a 4-tert-butyl-2,3,5,6-tetrafluorophenylbis(triflyl)methane are both obtained at a ratio of 1:1 (45% yield, respectively). Therefore, in this case, using 1.0 equivalent weight of t-BuLi and 0.5 equivalent weight of $Tf_2O$ completely suppresses the production of 4-tert-butyl-2,3,5,6-tetrafluorophenylbis(triflyl)methane, and a pentafluorophenylbis(triflyl)methane with $Tf_2O$ as a base can be obtained at a high yield.

In the metallic salt of the arylbis(perfluoroalkylsulfonyl)methane represented by the general formula [6] of the present invention [sometimes referred to as metallic arylbis(trifluoromethylsulfonyl)methide], $R^2$ shows a substituted or unsubstituted aryl group, $Rf^1$ and $Rf^2$ are independent to each other and show a perfluoroalkyl group, M shows any one of the elements selected from alkaline metallic element, alkaline earth metallic element, transition metallic element, silicon, germanium, tin, lead, arsenic, antimony, bismuth or tellurium, and n shows a numeric value equal to the valence of M element. Here, examples of the metal species of metallic arylbis(trifluoromethylsulfonyl)methide include, for example: alkaline metallic elements such as lithium, sodium, potassium, rubidium, cesium and francium; alkaline earth metallic element such as beryllium, magnesium, calcium, strontium, barium and radium; transition metallic elements such as scandium, yttrium, lanthanum, cerium, praseodymium, neodymium, promethium, samarium, europium, gadolinium, terbium, dysprosium, holmium, erbium, thulium, ytterbium, lutetium, titanium, zirconium, hafnium, vanadium, niobium, tantalum, chromium, molybdenum, tungsten, manganese, technetium, rhenium, iron, ruthenium, osmium, cobalt, rhodium, iridium, nickel, palladium, boron, aluminum, platinum, copper, silver, gold, zinc, cadmium and mercury; silicon; germanium; tin; lead; arsenic; antimony; bismuth or tellurium. Among these, lithium, scandium, silver, silicon and the like are especially preferable.

The $R^2$ in the formula [6] mentioned above is the same as the $R^2$ represented by the general formula [4] in the method for producing the arylbis(perfluoroalkylsulfonyl)methane of the present invention. The $Rf^1$ and $Rf^2$ in the general formula [6] mentioned above is the same as $Rf^1$ and $Rf^2$ in the arylbis(perfluoroalkylsulfonyl)methane represented by the general formula [1] and [4] of the present invention.

Specific examples of the metallic arylbis(perfluoroalkylsulfonyl)methide of the present invention include, for example, a metallic salt of phenylbis(triflyl)methane, a metallic salt of 2-naphthylbis(triflyl)methane, a metallic salt of 1-naphthylbis(triflyl)methane, a metallic salt of 2,4,6-trimethylphenylbis(triflyl)methane, a metallic salt of 4-(trifluoromethyl)phenylbis(triflyl)methane, a metallic salt of 3,5-bis(trifluoromethyl)phenylbis(triflyl)methane, a metallic salt of pentafluorophenylbis(triflyl)methane, a metallic salt of {4-(pentafluorophenyl)-2,3,5,6-tetrafluorophenyl}bis(triflyl)methane, and the like. Among these, the metallic salts such as lithium salt, scandium salt and the like are preferable, and the scandium salt and lithium salt of pentafluorophenylbis(triflyl)methane and {4-(pentafluorophenyl)-2,3,5,6-tetrafluorophenyl}bis(triflyl)methane are especially preferable in view of the catalytic activity and the like.

As to the method for producing the metallic arylbis(trifluoromethylsulfonyl)methide of the present invention, for example, the reactions of the arylbis(trifluoromethylsulfonyl)methane of the present invention mentioned above can be given as follows: (1) neutralization with a hydroxide of a metal, (2) reaction by heating under reflux with a salt or an oxide of a transition metal, and (3) reaction with a silver carbonate under shade. Further, another method which is the exchange reaction of metal species, can be exemplified, wherein a metallic salt such as a silver salt of the arylbis(perfluoroalkylsulfonyl)methane represented by the general formula [4], and a halide of a metal of different metal species are reacted. Specific examples of the hydroxide of the metal in the neutralization in (1) mentioned above include the hydroxide of alkaline metal such as lithium hydroxide, sodium hydroxide and potassium hydroxide, and the hydroxide of alkaline earth metal such as calcium hydroxide. A method wherein said arylbis(trifluoromethylsulfonyl)methane of the present invention is reacted for 10 minutes to over 10 hours by using a solution wherein the hydroxides of these metals are dissolved in a solvent such as diethylether and the like, can be exemplified. Specific examples of the salt or the oxide of the transition metal in the reaction by heating under reflux in (2) mentioned above include the lanthanoid metallic salt such as the chloride and the like of lanthanum and cerium, and scandium oxide such as $Sc_2O_3$ and the like. A method wherein heating under reflux in the aqueous solution is conducted for 10 minutes to over 10 hours can be exemplified.

The $R^2$ and $Rf^1$ and $Rf^2$ in the arylbis(perfluoroalkylsulfonyl)methane represented by the general forumula [4] in the method for producing the metallic arylbis(trifluoromethylsulfonyl)methide of the present invention show the same group as that of $R^2$ and $Rf^1$ and $Rf^2$ in the general formula [6] mentioned above. As a method for producing an arylbis(perfluoroalkylsulfonyl)methane, the method for producing the arylbis(trifluoromethylsulfonyl)methane in the method for producing the arylbis(trifluoromethylsulfonyl)methane of the present invention can be applied.

There is no limitation to the catalyst such as Lewis acid catalyst and the like comprising the metallic salt of arylbis(perfluoroalkylsulfonyl)methane of the present invention, as long as it is a catalyst that at least comprises a metallic salt of arylbis(perfluoroalkylsulfonyl)methane as an active ingredient. For example, a catalyst that is supported on a carrier, a catalyst that is fixed on a high polymer compound, and a catalyst having a surface active-ability by making a hydrophobic atomic group and a hydrophilic atomic group exist in the molecules, can be given as specific examples. These catalysts such as Lewis acid catalyst and the like comprising the metallic salt of arylbis(perfluoroalkylsulfonyl)methane have a catalytic activity that exceeds that of the existing Lewis acids, and therefore, they can be used for synthesis reaction of organic compounds in a high yield and with excellent selectivity.

The use of the catalyst such as Lewis acid catalyst and the like comprising the metallic salt of the arylbis(perfluoroalkylsulfonyl)methane mentioned above makes it possible to synthesize organic compounds such as pharmaceuticals, agricultural chemical, asymmetric catalyst, various types of functional materials, and the like. A specific example of said method for synthesizing is a method wherein a catalytic reaction is conducted under the presence of a catalyst such as Lewis acid catalyst or the like comprising the metallic salt of arylbis(perfluoroalkylsulfonyl)methane mentioned above in an aqueous solution, in an organic solvent or in a mixed solvent of water and organic solvent. Specific examples of the catalytic reaction mentioned above include a benzoylation reaction, a Diels-Alder reaction, an Algol-type reaction, a Friedel-Crafts reaction, a Mannich reaction, a glycosilation reaction, an esterification reaction, an ene reaction, a cationic polymerization reaction, an allylation reaction, an interesterification reaction, a Mannich-type reaction, a Michael addition reaction, an acylation reaction, a conjugate addition reaction, a dehydration reaction, a dehydration/condensation reaction, a polymerization reaction and the like.

The present invention will now be explained further in more details with the examples below, however, the scope of the invention is not limited to the exemplifications.

EXAMPLE 1

Analysis and Material

The infrared radiation spectrum was determined by using a Shimadzu FTIR-9100. The $^1$H NMR spectrum was determined by using a Varian Gemini-300 (300 MHz) nuclear magnetic resonance apparatus. The chemical shift of $^1$H NMR was indicated by ppm wherein a solvent as an internal standard (tetramethylsilane at 0 ppm) was used. The division pattern was shown as singlet: s, doublet: d, triplet: t, quartet: q, multiplet: m and broad peak: br. The $^{13}$C NMR spectrum was determined by using a Varian Gemini-300 (125 MHz) nuclear magnetic resonance apparatus, and was indicated by ppm wherein a solvent as an internal standard (CDCl$_3$ at 77.0 ppm) was used. The $^{19}$F NMR spectrum was determined by using a Varian Gemini-300 (282 MHz) nuclear magnetic resonance apparatus, and was indicated by ppm wherein a solvent as an internal standard (CF$_3$C$_6$H$_5$ at −64.0 ppm) was used. High-performance liquid chromatography (HPLC) analysis was conducted with a Shimadzu LC-10AD instrument and an SPD-M10A UV detector by using a chiral column (Daicel, AS or OD-H). All of the following examples were conducted in a glass instrument dried in an oven, by using a magnetic stirrer. The reaction product was purified on a Silica Gel E. Merck 9385 or a Silica Gel 60 Extra Pure by flash chromatography. High resolution mass spectrometry (HRMS) analysis was performed with the use of an instrument of Daikin Industries, Ltd.

EXAMPLE 2

Synthesis of Arylmethyl Triflone

Each of the mixed solutions of aryl halomethyl (10 mmol), sodium trifluoromethane sulfinate (2.0 g: 13 mmol), propionitrile (30 mL) and tetrabutyl ammonium iodide (0.37 g: 1 mmol), shown in Table 1, were subjected to heating under reflux in an argon atmosphere for approximately 1 day. After the heating under reflux, the reaction solutions were cooled to room temperature, and were concentrated after removing the salt by filtration. The crude products obtained were purified by silica gel column chromatography (developing solvent: hexane-EtOAc) or recrystallization operation (hexane-toluene) to obtain arylmethyl triflone. The yield of each of the arylmethyl triflone is indicated in Table 1, and the physical property of each of the arylmethyl triflone is shown below. Table 1 showed that when sodium trifluoromethane sulfonate (TfNa) used as an electrophilic reactant as a triflyl source, and heating under reflux with aryl halomethane was conducted by using propionitrile as a solvent under the presence of a tetrabutyl ammonium iodide catalyst, arylmethyl triflone can be obtained at a high yield than the method of Hendrickson et al. (Synthesis, 691, 1997).

TABLE 1

| aryl halomethane | arylmethyl triflone | [yield (%)] |
|---|---|---|
| PhCH$_2$Br | PhCH$_2$Tf | 94 |
| 2-NaphCH$_2$Br | 2-NaphCH$_2$Tf | >99 |
| 1-NaphCH$_2$Cl | 1-NaphCH$_2$Tf | 99 |
| 2,4,6-Me$_3$C$_6$H$_2$CH$_2$Cl | 2,4,6-Me$_3$C$_6$H$_2$CH$_2$Tf | 90 |
| 4-CF$_3$C$_6$H$_4$CH$_2$Br | 4-CF$_3$C$_6$H$_4$CH$_2$Tf | >99 |
| 3,5-(CF$_3$)$_2$C$_6$H$_3$CH$_2$Br | 3,5-(CF$_3$)$_2$C$_6$H$_3$CH$_2$Tf | 76 |
| C$_6$F$_5$CH$_2$Br | C$_6$F$_5$CH$_2$Tf | 89 |

Benzyl triflone (2-Benzyl Triflone; J. Fluorine Chem. 66, 301, 1994): IR (KBr) 1362, 1347, 1223, 1198, 1188, 1125, 776, 698, 640, 525, 507 cm$^{-1}$; $^1$H NMR (CDCl$_3$, 300 MHz) δ 4.48 (s, 2H), 7.42-7.47 (m, 5H); $^{19}$F NMR (CDCl$_3$, 282 MHz) δ−77.6 (s, 3F, CF$_3$).

2-naphthylmethyl triflone (2-Naphthylmethyl Triflone): IR (KBr) 1358, 1345, 1221, 1194, 1125, 831, 756, 658, 608, 486 cm$^{-1}$; $^1$H NMR (CDCl$_3$, 300 MHz) δ 4.65 (s, 2H), 7.50 (dd, J=1.8, 8.4 Hz, 1H), 7.54-7.58 (m, 2H), 7.86-7.94 (m, 4H); $^{13}$C NMR (CDCl$_3$, 125 MHz) δ 56.3, 119.8 (q, J$_{CF}$=326 Hz, 1C), 120.3, 126.9, 127.4, 127.5, 127.8, 128.1, 129.2, 131.5, 133.1, 133.6; $^{19}$F NMR (CDCl$_3$, 282 MHz) δ−77.6 (s, 3F, CF$_3$). Anal. Calcd. for C$_{12}$H$_9$O$_2$F$_3$S: C, 52.55; H, 3.31; F, 20.78; S, 11.69. Found C, 52.51; H, 3.33; F, 20.81; S, 11.65.

1-naphthylmethyl triflone (1-Naphthylmethyl Triflone): IR (KBr) 1510, 1358, 1223, 1200, 804, 776, 658, 486 cm$^{-1}$; $^1$H NMR (CDCl$_3$, 300 MHz) δ 4.99 (s, 2H), 7.53 (dd, J=7.8, 8.4 Hz, 1H), 7.62 (d, J=7.8 Hz, 1H), 7.58 (ddd, J=0.9, 6.9, 8.3 Hz, 1H), 7.65 (ddd, J=1.5, 6.9, 8.4 Hz, 1H), 7.93 (dd, J=1.5, 8.3 Hz, 1H), 7.98 (dd, J=8.4 Hz, 1H), 8.04 (dd, J=0.9, 8.4 Hz, 1H); $^{13}$C NMR (CDCl$_3$, 125 MHz) δ 53.0, 119.2, 120.0 (q, J$_{CP}$=326 Hz, 1C), 123.3, 125.3, 126.5, 127.5, 129.0, 131.1, 131.5, 132.3, 134.0; $^{19}$F NMR (CDCl$_3$, 282 MHz) δ−78.1 (s, 3F, CF$_3$). Anal. Calcd. for C$_{12}$H$_9$O$_2$F$_3$S: C, 52.55; H, 3.31; F, 20.78; S, 11.69. Found C, 52.53; H, 3.29; F, 20.75; S, 11.73.

2,4,6-trimethylphenylmethyl triflone (2,4,6-Trimethylphenylmethyl Triflone): IR (KBr) 1358, 1206, 1117, 864, 619, 550, 500, 469 cm$^{-1}$; $^1$H NMR (CDCl$_3$, 300 MHz) δ 2.29 (s, 3H), 2.43 (s, 6H) 4.62 (s, 2H), 6.96 (s, 2H); $^{13}$C NMR (CDCl$_3$, 125 MHz) δ 20.3, 21.0 (2C), 49.8, 117.0, 120.0 (q, J$_{CF}$=326 Hz, 1C, CF$_3$), 129.9 (2C), 139.7 (2C), 139.8; $^{19}$F NMR (CDCl$_3$, 282 MHz) δ−79.7 (s, 3F, CF$_3$). Anal. Calcd. for C$_{11}$H$_{13}$O$_2$F$_3$S: C, 49.62; H, 4.92; F, 21.40; S, 12.04. Found C, 49.58; H, 4.53; F, 21.35; S, 12.06.

4-(trifluoromethyl)phenylmethyl triflone (4-(Trifluoromethyl)phenylmethyl Triflone; Synthesis, 691, 1997): IR (KBr) 1356, 1341, 1227, 1210, 1144, 1121, 855, 658, 513 cm$^{-1}$; $^1$H NMR (CDCl$_3$, 300 MHz) δ 4.53 (s, 2H), 7.58 (d, J=8.0 Hz, 2H), 7.72 (d, J=8.0 Hz, 2H); $^{19}$F NMR (CDCl$_3$, 282 MHz) δ −77.5 (s, 3F, CF$_3$), −64.3 (s, 3F, CF$_3$).

3,5-bis(trifluoromethyl)phenylmethyl triflone (3,5-Bis(trifluoromethyl)phenylmethyl Triflone): IR (KBr) 1376, 1362, 1277, 1175, 1117, 918, 910, 669 cm$^{-1}$; $^1$H NMR (CDCl$_3$, 300 MHz) δ 4.60 (s, 2H), 7.91 (s, 2H), 8.01 (s, 1H); $^{13}$C NMR (CDCl$_3$, 125 MHz) δ 55.0, 119.6 (q, J$_{CF}$=326 Hz, 1C, CF$_3$), 122.6 (q, J$_{CF}$=272 Hz, 2C, 2CF$_3$), 124.2 (septet, J$_{CF}$=4 Hz, 1C), 126.1, 131.3 (2C), 132.9 (q, J$_{CF}$=34 Hz, 2C); $^{19}$F NMR (CDCl$_3$, 282 MHz) δ−77.4 (s, 3F, CF$_3$), −64.3 (s, 6F, 2CF$_3$). Anal. Calcd. for C$_{10}$H$_3$O$_2$F$_9$S: C, 33.53; H, 0.84; F, 47.74; S, 8.95. Found C, 33.48; H, 0.91; F, 47.87; S, 8.89.

Pentafluorophenylmethyl triflone (Pentafluorophenylmethyl Triflone): IR (KBr) 1509, 1374, 1210, 1121, 995 cm$^{-1}$; $^1$H NMR (CDCl$_3$, 300 MHz) δ 4.64; $^{13}$C NMR (CDCl$_3$, 125 MHz) δ 44.3, 100.0 (dt, J$_{CF}$=4, 17 Hz, 1C, ipso-C), 119.5 (q, J$_{CF}$=326 Hz, 1C, CF$_3$), 137.9 (d, J$_{CF}$=251 Hz, 2C, 2m-C), 142.8 (d, J$_{CF}$=258 Hz, 1C, p-C), 145.9 (d, J$_{CF}$=252 Hz, 2C, 2o-C); $^{19}$F NMR (CDCl$_3$, 282 MHz) δ−160.0 (d, J=15.2Hz, 2F, 2m-F), 149.0 (s, 1F, p-F), 139.4 (d, J=15.2 Hz, 2F, 2o-F), −78.3 (s, 3F, CF$_3$). Anal. Calcd. for C$_8$H$_2$O$_2$F$_8$S: C, 30.59; H, 0.64; F, 48.38; S, 10.21. Found C, 30.49; H, 0.73; F, 48.37; S, 10.18.

EXAMPLE 3

Examination of the Method for Synthesizing Arylbis(triflyl)methane

The benzyl triflone obtained from Example 2 (0.5 mmol) was dissolved in diethylether (3 mL), this solution was cooled to −78° C., then added with 2.2 equivalent weight (1.1 mmol) of t-BuLi (0.34 mL, 1.6 M pentane solution), and was stirred for 0.5 hour. Next, after Tf$_2$O (46 μL, 0.55 mmol) was added, the temperature of the reaction solution was raised to room temperature, and the solution was further stirred for 1 hour. Subsequently, water was added to stop the reaction, the solution was neutralized, and then washed with hexane. These aqueous phases were acidified with 4 M of hydrochloride, and were twice extracted with diethylether. The organic phase was dried, filtrated and concentrated with magnesium sulfate to obtain phenylbis(triflyl)methane [Ph- CHTf$_2$] as a solid (79% yield). However, only a small amount of phenyltris(triflyl)methane [PhCTf$_3$] was produced. Meanwhile, the same reaction as mentioned above, except for the use of 1.1 equivalent weight of t-BuLi instead of 2.2 equivalent weight of t-BuLi, was conducted, and the yield of PhCHTf$_2$ was 6% and that of PhCTf$_3$ was 46%.

EXAMPLE 4

Synthesis of Arylbis(triflyl)methane

Each of the arylmethyl triflone (0.5 mmol) obtained from Example 2 were dissolved in diethylether (3 mL), and their solutions were prepared, respectively. These solutions were cooled to −78° C., then added with 1.1 equivalent weight (0.55 mmol) of t-BuLi (0.34 mL, 1.6 M pentane solution), and were stirred for 10 minutes. Next, Tf$_2$O (46 µL, 0.275 mmol) was added, the temperature of the reaction solution was raised to room temperature, and the solution was further stirred for 1 hour. After cooling the solution again to −78° C., 1.1 equivalent weight (0.55 mmol) of t-BuLi (0.34 mL, 1.6 M pentane solution) was added, and the solution was stirred for 10 minutes. Subsequently, Tf$_2$O (46 µL, 0.275 mmol) was added, the temperature of the reaction solution was raised to room temperature, and the solution was further stirred for 1 hour. Then, water was added to stop the reaction, the solution was neutralized, and then washed with hexane. These aqueous phases were acidified with 4 M of hydrochloride, and were twice extracted with diethylether. The organic phase was dried, filtrated and concentrated with magnesium sulfate to obtain arylbis(triflyl)methane as a solid. No further purification was needed. The yield of each of the arylmethyl triflone is indicated in Table 2, and the physical property of each of the arylmethyl triflone is shown below.

TABLE 2

| arylmethyl triflone | arylbis(triflyl)methane | [yield (%)] |
| --- | --- | --- |
| 2-NaphCH$_2$Tf | 2-NaphCHTf$_2$ | 84 |
| 1-NaphCH$_2$Tf | 1-NaphCHTf$_2$ | 98 |
| 2,4,6-Me$_3$C$_6$H$_2$CH$_2$Tf | 2,4,6-Me$_3$C$_6$H$_2$CHTf$_2$ | 89 |
| 4-CF$_3$C$_6$H$_4$CH$_2$Tf | 4-CF$_3$C$_6$H$_4$CHTf$_2$ | 87 |
| 3,5-(CF$_3$)$_2$C$_6$H$_3$CH$_2$Tf | 3,5-(CF$_3$)$_2$C$_6$H$_3$CHTf$_2$ | 75 |
| C$_6$F$_5$CH$_2$Tf | C$_6$F$_5$CHTf$_2$ | 45 |

Phenylbis(triflyl)methane (Phenylbis(triflyl)methane; J. Org. Chem. 38, 3358, 1973; Heteroatom Chem. 5, 9, 1994): IR (KBr) 2950, 1381, 1242, 1219, 1184, 1102, 806, 695, 660, 608, 585; 507 cm$^{-1}$; $^1$H NMR (CDCl$_3$, 300 MHz) δ 5.97 (s, 1H), 7.54-7.68 (m, 5H); $^{13}$C NMR (CDCl$_3$, 125 MHz) δ 80.7, 119.3, 119.3 (q, J$_{CF}$=329 Hz, 2C, 2CF$_3$), 130.0 (2C), 131.8 (br), 132.9 (2C); $^{19}$F NMR (CDCl$_3$, 282 MHz) −73.8 (s, 6F, 2CF$_3$).

2-naphthylbis(triflyl)methane (2-Naphthylbis(triflyl)methane): IR (KBr) 1393, 1381, 1244, 1213, 1103, 646, 586 cm$^{-1}$; $^1$H NMR (CDCl$_3$, 300 MHz) δ 6.10 (s, 1H), 7.61-7.71 (m, 3H), 7.92-7.99 (m, 2H), 8.03 (d, J=8.4 Hz, 2H); $^{13}$C NMR (CDCl$_3$, 75 MHz) δ 80.9, 116.3, 119.3 (q, J$_{CF}$=329 Hz, 2C, 2CF$_3$), 127.7, 128.0, 128.8, 129.1, 130.1, 132.8, 133.4, 134.7; $^{19}$F NMR (CDCl$_3$, 282 MHz) δ−73.6 (s, 6F, 2CF$_3$); HRMS (EI) calcd for C$_{13}$H$_8$O$_4$F$_6$S$_2$ [M]$^+$ 405.9768, found 405.9761.

1-naphthylbis(triflyl)methane (1-Naphthylbis(triflyl)methane): IR (KBr) 1389, 1383, 1215, 1111, 770, 650, 504 cm$^{-1}$; $^1$H NMR (CDCl$_3$, 300 MHz) δ 6.87 (s, 1H), 7.62-7.80 (m, 4H), 8.02 (d, J=8.4 Hz, 1H), 8.16 (d, J=8.4 Hz, 1H), 8.37 (d, J=7.5 Hz, 1H); $^{13}$C NMR (CDCl$_3$, 75 MHz) δ 74.6, 114.1 (s, 1C, ipso-C), 119.4 (q, J$_{CF}$=328 Hz, 2C, 2CF$_3$), 119.9, 125.4, 127.0, 128.9, 130.1, 131.5, 131.7. 133.8, 134.0; $^{19}$F NMR (CDCl$_3$, 282 MHz) δ−74.2 (s, 6F, 2CF$_3$); HRMS (EI) calcd for C$_{13}$H$_8$O$_4$F$_6$S$_2$ [M]$^+$ 405.9768, found 405.9761.

2,4,6-trimethylphenylbis(triflyl)methane (2,4,6-Trimethylphenylbis(triflyl)methane): IR (KBr) 1397, 1383, 1217, 1119, 1107, 642, 590 cm$^{-1}$; $^1$H NMR (CDCl$_3$, 300 MHz) δ 2.33 (s, 3H), 2.35 (s, 3H), 2.61 (s, 3H), 6.48 (s, 1H), 7.00 (s, 1H), 7.08 (2, 1H); $^{13}$C NMR (CDCl$_3$, 75 MHz) δ 20.2, 21.1, 22.2, 77.7, 115.9, 119.4 (q, J$_{CF}$=328 Hz, 2C, 2CF$_3$), 130.4, 132.2, 140.0, 142.2, 142.6; $^{19}$F NMR (CDCl$_3$, 282 MHz) δ−76.3 (s, 6F, 2CF$_3$); HRMS (EI) calcd for C$_{12}$H$_{12}$O$_4$F$_6$S$_2$ [M]$^+$ 398.0081, found 398.0089.

4-(trifluoromethyl)phenylbis(triflyl)methane (4-(Trifluoromethyl)phenylbis(triflyl)methane): IR (KBr) 1393, 1383, 1327, 1231, 1171, 1136, 1111, 860, 671, 610 cm$^{-1}$; $^1$H NMR (CDCl$_3$, 300 MHz) δ 5.98 (s, 1H), 7.84 (s, 4H); $^{13}$C NMR (CDCl$_3$, 125 MHz) δ 80.4, 120.0 (q, J$_{CF}$=329 Hz, 2C, 2CF$_3$), 123.8 (q, J$_{CF}$=271 Hz, 1C, CF$_3$), 124.2, 127.6 (q, J=4 Hz, 2C), 133.0 (2C), 135.6 (q, J$_{CF}$=33 Hz, 1C); $^{19}$F NMR (CDCl$_3$, 282 MHz) δ−73.5 (s, 6F, 2CF$_3$), −64.7 (s, 3F, CF$_3$); HRMS (EI) calcd. for C$_{10}$H$_5$O$_4$F$_9$S$_2$ [M]$^+$ 423.9486, found 423.9471.

3,5-bis(trifluoromethyl)phenylbis(triflyl)methane (3,5-Bis(trifluoromethyl)phenylbis(triflyl)methane): IR (KBr) 1395, 1374, 1285, 1223, 1194, 1179, 1144, 1105, 936, 909, 629, 519 cm$^{-1}$; $^1$H NMR (CDCl$_3$, 300 MHz) δ 6.05 (s, 1H), 8.13 (s, 2H), 8.18 (s, 1H); $^{13}$C NMR (CDCl$_3$, 125 MHz) δ 78.9, 119.2 (q, J$_{CF}$=329 Hz, 2C, 2CF$_3$), 122.2 (q, J$_{CF}$=272 Hz, 2C, 2CF$_3$), 122.9, 126.7 (septet, J$_{CF}$=4 Hz), 131.6 (s, 2C), 133.8 (q, J=35 Hz, 2C); $^{19}$F NMR (CDCl$_3$, 282 MHz) δ−73.2 (s, 6F, 2CF$_3$), −64.3 (s, 6F, 2CF$_3$); HRMS (EI) calcd for C$_{11}$H$_4$O$_4$F$_{12}$S$_2$ [M]$^+$ 472.9375, found 472.9372.

Pentafluorophenylbis(triflyl)methane (Pentafluorophenylbis(triflyl)methane): Mp. 86° C. to 87° C.; IR (KBr) 1522, 1501, 1347, 1321, 1198, 1127, 1024, 988, 613 cm$^{-1}$; $^1$H NMR (CDCl$_3$, 300 MHz) δ 6.21 (brs, 1H); $^{13}$C NMR (CDCl$_3$, 125 MHz) δ 70.4, 98.0 (s, 1C, ipso-C), 119.2 (q, J$_{CF}$=330 Hz, 2C, 2CF$_3$), 137.8 (d, J$_{CF}$=258 Hz, 1C, m-C), 138.6 (d, J$_{CF}$=257 Hz, 1C, m-C), 144.7 (d, J$_{CF}$=264 Hz, 1C, p-C), 145.4 (d, J$_{CF}$=262 Hz, 1C o-C), 147.2 (d, J$_{CF}$=262 Hz, 1C, o-C); $^{13}$C NMR (CD$_3$OD (δ49.0), 125 MHz) δ 56.2, 109.1 (dt, J=6, 19 Hz, 1C, ipso-C), 122.4 (q, J$_{CF}$=324 Hz, 2C, 2CF$_3$) 138.5 (d, J$_{CF}$=250 Hz, 2C, 2m-C), 143.0 (d, J$_{CF}$=251 Hz, 1C, p-C), 150.0 (d, J$_{CF}$=245 Hz, 1C, o-C); $^{19}$F NMR (CDCl$_3$, 282 MHz) δ−157.9 (dt, J=6.2, 21.5 Hz, 1F, m-F), −156.8 (dt, J=6.2, 21.5 Hz, 1F, m-F), −142.6 (tt, J=5.9, 21.5 Hz, 1F, p-F), −140.3 (br, 1F, o-F), −127.7 (ddd, J=5.9, 15.2, 21.5 Hz, 1F, o-F), −75.2 (s, 6F, 2CF$_3$); HRMS (EI) calcd. for C$_9$HO$_4$F$_{11}$S$_2$ [M]$^+$ 445.9141, found 445.9137.

EXAMPLE 5

Nucleophilic Substitution Specific to the Para Position of Pentafluorophenylbis(triflyl)methane As it is described in Table 2 that the yield of pentafluorophenylbis(triflyl)methane is 45%, it was revealed that when pentafluorophenylbis(triflyl)methane is produced using a pentafluoromethylbromide, both of pentafluorophenylbis(triflyl)methane and 4-tert-butyl-2,3,5,6-tetrafluorophenylbis(triflyl)methane can be obtained at a ratio of 1:1 (45% yield, respectively). However, it was found out that when 1.0 equivalent weight of t-BuLi and 0.5 equivalent weight of Tf$_2$O are used, the production of 4-tert-butyl-2,3,5,6-tetrafluorophenylbis(triflyl)methane is completely suppressed, and pentafluorophenylbis(triflyl)methane can be obtained at 95% yield with Tf₂O as a base. Consequently, the reactions of pentafluorophenylbis(triflyl)methane with the various types of alkyl lithium reagents were examined, in order to determine the generality and range of the nucleophilic substitution specific to the para position of pentafluorophenylbis(triflyl)methane. Table 3 shows the types of alkyl lithium reagents, the reaction conditions and the yield of the para position substituents of pentafluorophenylbis(triflyl)methane. The para position substituents of pentafluorophenylbis(triflyl)methane shown in Table 3 are obtained by washing the reaction product obtained by reacting pentafluorophenylbis(triflyl)methane with alkyl lithium reagent, with a hydrochloric solution. The "Bn" shown in Table 3 represents a benzyl group.

TABLE 3

| RLi (equivalent weight) | Condition | 5, yield (%) |
|---|---|---|
| t-BuLi (3) | −78° C., 1 h | 87 |
| BuLi (3) | −78° C., 1 h | >95 |
| BnLi (5) | −78° C., 6 h | 83 |
| PhLi (3) | −78° C. to rt, 1 day | >95 |
| 3,4,5-F₃C₆H₂Li (5) | −20° C. to rt, 3 h | 75 |
| 3,5-(CF₃)₂C₆H₃Li (5) | −20° C. to rt, 3 h | 70 |

EXAMPLE 6

Synthesis of {4-(pentafluorophenyl)-2,3,5,6-tetrafluorophenyl}bis(triflyl)methane Synthesis of 4-methylperfluorobiphenyl;

A diethylether solution of methyl lithium (13 mL, 15 mmol) was dropped for 0.5 hour to a THF (50 mL) solution dissolved with perfluorobiphenyl (10 g, 30 mmol), at −78° C. under argon atmosphere. Then, after the solution was stirred at the same temperature for 2 hours, it was further stirred at room temperature for 2 hours. Water was added to stop the reaction, diethylether was used for extraction, and its organic phase was dried with magnesium sulfate. After filtration was conducted, the solvent was removed under reduced pressure, and a mixture of 4-methylperfluorobiphenyl, 4,4'-dimethylperfluorobiphenyl and perfluorobiphenyl (molar ratio, 30:3:67) was obtained as a crude product.

Synthesis of 4-(bromomethyl)perfluorobiphenyl;

A mixed solution of a mixture comprising the 4-methylperfluorobiphenyl mentioned above, an N-bromo succinimide (NBS) (26.7 g, 150 mmol), AIBN (0.99 g, 6 mmol) and a carbon tetrachloride (100 mL) was subjected to heating under reflux for 1 week. During this process, the progress of the reaction was confirmed by TLC, and NBS and AIBN were added on a timely basis. Ultimately, 285 mmol NBS and 15 mmol AIBN were added to the solution. After the reaction was completed, the solution was cooled to room temperature, and the solvent was removed under reduced pressure. The crude product was purified by silica gel column chromatography (developing solvent: hexane-ethyl acetate=100:1), and the 4-(bromomethyl)perfluorobiphenyl (7.36 g, 18 mmol, total yield from methyl lithium 60%) was isolated. $^1$H NMR (CDCl₃, 300 MHz) δ 4.58 (s, 2H, CH₂Br); $^{19}$F NMR (CDCl₃, 282 MHz) δ−138.02 (dd, J=10.6, 19.8 Hz, 2F), −138.56 (dt, J=9.1, 20.3 Hz, 2F), −142.36 (dd, J=10.6, 19.8 Hz, 2F), −150.59 (t, J=20.3 Hz, 1F), −161.08 (dt, J=7.1, 20.3 Hz, 2F).

Synthesis of {4-(pentafluorophenyl)-2,3,5,6-tetrafluorophenyl}(triflyl)methane;

4-bromomethylperfluorobiphenyl (3.68 g, 9 mmol) and sodium trifluoromethane sulfinate (1.69 g, 10.8 mmol) were dissolved in propionitrile (30 mL), and the resultant solution was subjected to heating under reflux for 12 hours. After the reaction, the solution was cooled to room temperature, and water was added for extraction with ethyl acetate. The organic phase was dried with magnesium sulfate, filtrated, and the solvent was removed under reduced pressure. The crude product was purified by silica gel column chromatography (hexane-ethyl acetate=20:1 to 8:1 to 1:1), and the aimed {4-(pentafluorophenyl)-2,3,5,6-tetrafluorophenyl}(triflyl)methane (3.91 g, 8.46 mmol, 94% yield) was isolated. $^1$H NMR (CDCl₃, 300 MHz) δ 4.75 (s, 2H, CH₂Tf); $^{19}$F NMR (CDCl₃, 282 MHz) δ−78.24 (s, 3F, CF₃), −136.82 to −136.62 (m, 1F), −137.72 (dd, J=10.7, 18.3 Hz, 2F), −138.84 (dd, J=10.7, 18.3 Hz, 2F), −149.69 (t, J=21.3 Hz, 1F), −160.63 (dt, J=6.1, 21.3 Hz, 2F).

Synthesis of {4-(pentafluorophenyl)-2,3,5,6-tetrafluorophenyl}bis(triflyl)methane;

A tert-butyl magnesium chloride (5 mL, 10 mmol, 2.0 M diethylether solution) was added to a diethylether (120 mL) solution dissolved with {4-(pentafluorophenyl)-2,3,5,6-tetrafluorophenyl}(triflyl)methane (4.6 g, 10 mmol), at −78° C. under argon atmosphere. After the reaction solution was stirred for 0.5 hour at −78° C., it was further stirred for 0.5 hour at 0° C. Then, the solution was cooled again to −78° C., trifluoromethane sulfinic acid anhydride (0.84 mL, 5 mmol) was added, and the resultant solution was stirred for 2 hours at room temperature. Further, tert-butyl magnesium chloride (3.75 mL, 7.5 mmol, 2.0 M diethylether solution) was added at −78° C. After the reaction solution was stirred at −78° C. for 0.5 hour, it was stirred at 0° C. for 0.5 hour. The solution was cooled again to −78° C., trifluoromethanesulfonic acid anhydride (0.84 mL, 5 mmol) was added, and the resultant solution was stirred for 2 hours at room temperature. After the reaction was completed, water was added, further neutralized with 1 M hydrochloric acid water, and the water phase was washed with hexane. Then, said water phase was acidified with 4 M hydrochloric acid water, and extracted with diethylether. The organic phase was dried with magnesium sulfate, filtrated, and the solvent was removed under reduced pressure. The crude product was sublimated (8 to 9 Pa, 150° C., and the aimed {4-(pentafluorophenyl)-2,3,5,6-tetrafluorophenyl}bis(triflyl)methane (2.79 g, 4.7 mmol, 47% yield) was isolated. $^1$H NMR (CDCl₃, 300 MHz) δ 6.32 (s, 1H, CH), $^{19}$F NMR (CDCl₃, 282 MHz) δ−75.1 (s, 6F, 2CF₃), −127.72 to −127.58 (m, 1F), −133.43 (dt, J=10.2, 21.3 Hz, 1F), −134.60 (dt, J=9.4, 21.3 Hz, 1F), −137.08 to −137.35 (m, 2F), −140.07 (br, 1F), −148.38 (t, J=21.3 Hz, 1F), −160.01 (dt, J=6.2, 21.3 Hz, 2F).

EXAMPLE 7

Synthesis of 4' Position Alkyl Substituent of {4-(pentafluorophenyl)-2,3,5,6-tetrafluorophenyl}bis(triflyl)methane Phenyl lithium (0.28 mL, 0.3 mmol, 1.06 M cyclohexane-diethylether mixed solution) was added to a diethylether (1 mL) solution dissolved with {4-(pentafluorophenyl)-2,3,5, 6-tetrafluorophenyl}bis(triflyl)methane (59 mg, 0.1 mmol), at −78° C. under argon atmosphere. The temperature of the reaction solution was slowly raised to −40° C., and the solution was stirred for 1 hour. Water was added to stop the reaction, the solution was neutralized with 1 M hydrochloric acid water, and the water phase was washed with hexane. Subsequently, the solution was acidified with 4 M hydrochloric acid water, and extracted with diethylether. The organic phase was dried with magnesium sulfate, filtrated, and the solvent was removed under reduced pressure. The product obtained thereby was the aimed compound, {4-(4-phenyl-2,3,5,6-tetrafluorophenyl)-2,3,5,6-tetrafluorophenyl}bis(triflyl)methane (57.2 mg, 0.088 mmol, 88% yield), and no further purification was required. $^1$H NMR (CDCl$_3$, 300 MHz) δ 6.33 (s, 1H, CH), 7.54 (s, 5H, C$_6$H$_5$); $^{19}$F NMR (CDCl$_3$, 282 MHz) δ−75.15 (s, 6F, 2CF$_3$), −128.03 (dt, J=10.5, 21.2Hz, 1F), −133.35 (dt, J=10.5, 21.2 Hz, 1F), −134.52 (dt, J=10.5, 21,2 Hz, 1F), −138.73 to −138.53 (m, 2F), −140.42 (br, 1F), −142.66 to −142.53 (m, 2F).

EXAMPLE 8

Synthesis of 4' Position Alkoxy Substituent of {4-(pentafluorophenyl)-2,3,5,6-tetrafluorophenyl}bis(triflyl)methane Hexanol (1.5 mL, 12 mmol) was added to a pyridine (10 mL) solution dissolved with 60% sodium hydride containing mineral oil (0.56 g, 14 mmol) at 0° C., and the resultant solution was stirred for 1 hour at room temperature. After the solution was cooled to −20° C., {4-(pentafluorophenyl)-2,3,5,6-tetrafluorophenyl}bis(triflyl)methane (1.2 g, 2 mmol) was added. The reaction solution was stirred at −20° C. for 5 hours. After the reaction, the solution was acidified with 4 M hydrochloric acid water, and was extracted with diethylether. After drying with magnesium sulfate, the solution was filtrated, and the solvent was removed under reduced pressure. The crude product was purified by sublimation (0.2 to 0.3 torr, 80° C.), and {4-(4-hexanoxy-2,3,5,6-tetrafluorophenyl)-2,3,5,6-tetrafluorophenyl}bis(triflyl)methane was obtained at 94% yield (1.27 g, 1.88 mmol). $^1$H NMR (CDCl$_3$, 300 MHz) δ 0.83 to 0.94 (m, 3H), 1.26 (br, 2H), 1.33 to 1.38 (m, 2H), 1.45 to 1.52 (m, 2H), 1.84 (5, J=6.8 Hz, 2H), 4.38 (t, J=6.8 Hz, 2H), 4.32 (s, 1H); $^{19}$F NMR (CDCl$_3$, 282 MHz) δ−75.0 (s, 6F, 2CF$_3$), −128.4 to −128.3 (m, 1F), −133.6 (dt, J=9.1, 21.3 Hz, 1F), −134.8 (dt, J=9.1, 21.3 Hz, 1F), −139.8 to −139.6 (m, 2F), −140.7 (br, 1F), −156.5 (d, J=19.7 Hz, 2F).

EXAMPLE 9

Synthesis of Para Position Alkoxy Substituent of Pentafluorophenylbis(triflyl)methane Hexanol (1.5 mL, 12 mmol) was added to a pyridine (10 mL) solution dissolved with 60% sodium hydride containing mineral oil (0.56 g, 14 mmol) at 0° C., and the resultant solution was stirred for 1 hour at room temperature. After the solution was cooled to −20° C., pentafluorophenylbis(triflyl)methane (0.89 g, 2 mmol) was added. The reaction solution was stirred at −20° C. for 5 hours. After the reaction, the solution was acidified with 4 M hydrochloric acid water, and was extracted with diethylether. After drying with magnesium sulfate, the solution was filtrated, and the solvent was removed under reduced pressure. The crude product was purified by sublimation (0.2 to 0.3 torr, 65° C.), and 4-hexanoxy-2,3,5,6-tetrafluorophenylbis(triflyl)methane was obtained at 99% yield (1.02 g, 1.98 mmol). $^1$H NMR (CDCl$_3$, 300 MHz) δ 0.91 (t, J=7.1 Hz, 3H), 1.32 to 1.37 (m, 4H), 1.43 to 1.51 (m, 2H), 1.83 (quintet, J=6.8 Hz, 2H), 4.44 (t, J=6.8 Hz, 2H), 6.19 (s, 1H); $^{19}$F NMR (CDCl$_3$, 282 MHz) δ−75.35 (s, 6F, 2CF$_3$), −130.64 (dt, J=9.9, 21.2 Hz, 1F), −143.16 (br, 1F), −155.31 (d, J=21.2 Hz, 1F).

EXAMPLE 10

Synthesis of Lithium Pentafluorophenylbis(triflyl)methide

The pentafluorophenylbis(triflyl)methane obtained from Example 4 (1 mmol) and LiOH·H$_2$O (1 mmol) were dissolved in a diethylether (10 mL), the resultant solution was stirred at room temperature for 12 hours, then concentrated and dried to obtain a white powder, lithium pentafluorophenylbis(triflyl)methide (100% yield). The physical property of this lithium pentafluorophenylbis(triflyl)methide obtained is as follows.

Lithium pentafluorophenylbis(triflyl)methide (Lithium Pentafluorophenylbis(triflyl)methide): $^{13}$C NMR (CD$_3$OD, 125 MHz) δ 56.1, 109.0 (dt, J=4, 19 Hz, 1C, ipso-C), 122.3 (q, J$_{CF}$=324 Hz, 2C, 2CF,), 138.5 (d, J$_{CF}$=247 Hz, 2C, 2m-C), 143.0 (d, J$_{CF}$=251 Hz, 1C, p-C), 149.5 (d, J$_{CF}$=245 Hz, 2C, 2o-C).

EXAMPLE 11

Synthesis of Lithium{4-(pentafluorophenyl)-2,3,5,6-tetrafluorophenyl}bis(triflyl)methide The {4-(pentafluorophenyl)-2,3,5,6-tetrafluorophenyl}bis(triflyl)methane obtained from Example 6 (1 mmol) and LiOH·H$_2$O (1 mmol) were dissolved in a diethylether (10 mL), the resultant solution was stirred at room temperature for 12 hours, then concentrated and dried to obtain a white solid, lithium{4-(pentafluorophenyl)-2,3,5,6-tetrafluorophenyl}bis(triflyl)methide (100% yield).

EXAMPLE 12

Synthesis of Silver (I) Pentafluorophenylbis(triflyl)methide

Ag$_2$CO$_3$ (66 mg, 0.24 mmol) was added to an aqueous solution (3 mL) of pentafluorophenylbis(triflyl)methane (0.20 g, 0.40 mmol) in a reaction flask wherein light was shut out by an aluminum foil. The solution was stirred at room temperature for 12 hours, then filtrated if there were any solid remaining, followed by concentration. A white solid of silver (I) pentafluorophenylbis(triflyl)methide was obtained thereby (99% yield or more). The physical property of this silver (I) pentafluorophenylbis(triflyl)methide obtained is as follows.

Silver (I) pentafluorophenylbis(triflyl)methide (Silver(I) Pentafluorophenylbis(triflyl)methide): $^{19}$F NMR (CDCl$_3$, 282 MHz) δ−162.6 (dt, J=7.6, 21.4 Hz, 2F, 2m-F), −150.6 (t, J=21.4 Hz, 1F, p-F), −134.7-134.6 (m, 2F, 2o-F), −79.5 (s, 6F, 2CF$_3$).

EXAMPLE 13

Synthesis of Scandium (III) Pentafluorophenylbis(triflyl)methide (Part 1)

Sc$_2$O$_3$ (21 mg, 0.155 mmol) and pentafluorophenylbis(triflyl)methane (0.277 g, 0.62 mmol) were subjected to heating under reflux in water (0.5 mL) for 12 hours. Then, the unreacted Sc$_2$O$_3$ was removed by filtration and condensation was conducted. The crude product obtained was washed with chloroform, the unreacted pentafluorophenylbis(triflyl)methane was removed, pressure was reduced by a vacuum pump, and then dried at 100° C. to obtain a white powder of scandium (III) pentafluorophenylbis(triflyl)methide (50% yield).

EXAMPLE 14

Synthesis of Scandium (III) Pentafluorophenylbis(triflyl)methide (Part 2)

The silver (I) pentafluorophenylbis(triflyl)methide obtained from Example 12 (0.19 g, 0.34 mmol) and Sc (III) Cl$_3$·(H$_2$O)$_6$ (29 mg, 0.11 mmol) were stirred in a diethylether (3 mL) at room temperature for 12 hours. Then, silver chloride was removed by filtration and condensation was conducted. The unreacted pentafluorophenylbis(triflyl) methane was removed, pressure was reduced by a vacuum pump, and then dried at 100° C. to obtain a white powder of scandium (III) pentafluorophenylbis(triflyl)methide (50% yield). The physical property of the scandium (III) pentafluorophenylbis(triflyl)methide obtained from the present Example and Example 13 is as follows.

Scandium (III) pentafluorophenylbis(triflyl)methide (Scandium(III) Pentafluorophenylbis(triflyl)methide): Mp.>250° C. (decomposed); $^{13}$C NMR (CD$_3$OD (δ 49.0), 125 MHz) δ 56.2, 109.0 (dt, J$_{CF}$=2, 20 Hz, 1C, ipso-C), 122.3 (q, J$_{CF}$=324 Hz, 2C, 2CF$_3$), 137.8 (d, J$_{CF}$=247 Hz, 2C, 2m-C), 142.3 (d, J$_{CF}$=251 Hz, 1C, p-C), 148.9 (d, J$_{CF}$=245 Hz, 2C, 2o-C); $^{19}$F NMR (CD$_3$OD, 282 MHz) δ−166.4 (dt, J=6.1, 21.3 Hz, 2F, 2m-F), −155.9 (t, J=21.3 Hz, 1F, p-F), −134.9 to −134.9 (m, 2F, 2o-F), −80.9 (s, 6F, 2CF$_3$).

EXAMPLE 15

Benzoylation Reaction of Menthol

Benzoylation reaction was conducted to a menthol wherein the scandium (III) pentafluorophenylbis(triflyl)methide obtained from Examples 13 and 14 was used as a Lewis acid catalyst (Chemical formula 38). l-menthol (0.18 g, 1 mmol) and benzoic anhydride (0.34 g, 1.5 mmol) were reacted while stirring in acetonitrile (4.8 mL) at 26° C. for 1 day, under the presence of the scandium (III) pentafluorophenylbis(triflyl)methide as 1 mol % of Lewis acid catalyst. Two to 3 drops of triethylamine was added to stop the reaction, the solution was added with 5 mL water, then concentrated and dried, and the menthyl benzoate produced was extracted with diethylether. The organic phase was analyzed with $^1$HNMR and it was found that the menthyl benzoate showed a high yield of 79%. The same reaction as mentioned above was conducted, except for the use of scandium (III) triflate [Sc(OTf)$_3$] as a conventionally known Lewis acid catalyst, instead of the scandium (III) pentafluorophenylbis(triflyl)methide mentioned above. The yield of menthyl benzoate was only 48%. Based on these results, it was found out that the catalytic activity of the scandium (III) pentafluorophenylbis(triflyl)methide of the present invention is much more higher compared to that of the existing Lewis acid catalysts.

(Chemical formula 20)

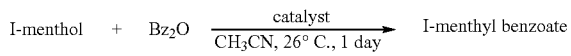

EXAMPLE 16

Diels-Alder Reaction of Methacrolein

Diels-Alder reaction was conducted to a methacrolein wherein the scandium (III) pentafluorophenylbis(triflyl)methide obtained from Examples 13 and 14 was used as a Lewis acid catalyst (Chemical formula 39). Methacrolein (0.21 mL, 2.6 mmol) and cyclopentadiene (0.56 mL, 6.8 mmol) were reacted while stirring in 3 mL dichloromethane at −40° C. for 4 hours, under the presence of scandium (III) pentafluorophenylbis(triflyl)methide as 1 mol % of Lewis acid catalyst. Two to 3 drops of triethylamine was added to stop the reaction, 5 mL of water was added and the 5-norbornene-2-aldehyde produced was extracted with pentane. After concentration and drying, the crude product was analyzed with $^1$HNMR and it was found that the 5-norbornene-2-aldehyde showed a high yield of 95% (88% exo). The same reaction as mentioned above was conducted, except for the use of scandium (III) triflate [Sc(OTf)$_3$] as a conventionally known Lewis acid catalyst, instead of the scandium (III) pentafluorophenylbis(triflyl)methide mentioned above. The 5-norbornene-2-aldehyde was hardly synthesized. Subsequently, 2 mol % of this scandium (III) triflate was used, and the yield of the 5-norbornene-2-aldehyde was 97% (89% exo). Based on these results, it was found out that the catalytic activity of the scandium (III) pentafluorophenylbis(triflyl)methide of the present invention is much more higher compared to that of the existing Lewis acid catalysts.

(Chemical formula 21)

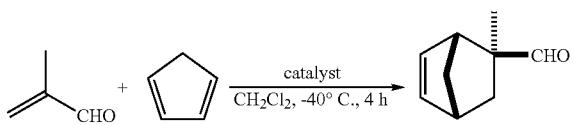

As can be seen from the Examples 5 and 9 and Examples 7 and 8 mentioned above, alkyl lithium generates a nucleophilic substitution reaction specifically to the para position of pentafluorophenylbis(triflyl)methane, whereas a nucleophilic substitution reaction is generated selectively at the 4' position when reacted with {4-(pentafluorophenyl)-2,3,5,6-tetrafluorophenyl}bis(triflyl)methane. Further, it was found out that as a nucleophilic reactant, not only limited to alkyl anion such as alkyl lithium and the like, alkoxy anion also shows the same reactivity. Moreover, as can be seen from the structural formula shown below and the pKa value (acetic acid) represented by the numeric value below the formula, when the para position of pentafluorophenylbis(triflyl)methane is substituted by an electron-donating group such as the alkyl group or the alkoxy group, its acidity decreases. However, when the same substituent was introduced to the 4' position of {4-(pentafluorophenyl)-2,3,5,6- tetrafluorophenyl}bis(triflyl)methane, its acidity did not decrease. This fact reveals that the super strong acidity of {4-(pentafluorophenyl)-2,3,5,6-tetrafluorophenyl}bis(triflyl)methane can be maintained even when it is supported on a resin or the like, with the use of the nucleophilic substitution reaction to the 4' position of {4-(pentafluorophenyl)-2,3,5,6-tetrafluorophenyl}bis(triflyl)methane. It shows that the {4-(pentafluorophenyl)-2,3,5,6-tetrafluorophenyl}bis(triflyl)methane is very useful as a synthesis material for various organic materials and acid catalysts with the use of super strong acidity.

(Chemical formula 22)

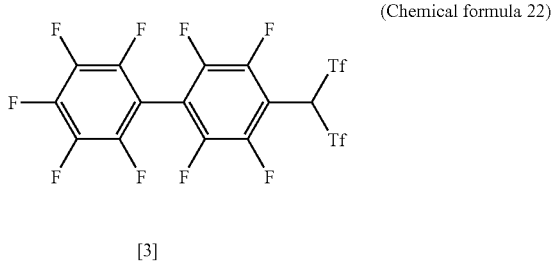

[3]

INDUSTRIAL APPLICABILITY

An arylbis(triflyl)methane having strong acidity can be produced efficiently and easily by the method for production according to the present invention. Since the pentafluorophenylbis(triflyl)methane and the like of the present invention are organic acids that are stronger than TfOH, their use as a novel type of conjugate base of protonic acid or metallic salt is expected. Moreover, since various types of aryl group can be introduced for an aryl group of arylbis(triflyl)methane, a wide application to asymmetric catalyst, functional material and the like is possible.

Further, the metallic arylbis(perfluoroalkylsulfonyl)methide such as scandium (III) pentafluorophenylbis(triflyl) methide and the like of the present invention shows a much better catalytic activity compared to that of the existing Lewis acid catalysts, and an organic compound can be easily synthesized at a high yield. The aryl group of metallic arylbis(perfluoroalkylsulfonyl)methide of the present invention can be introduced with various types of aryl group, and therefore, a wide application to asymmetric catalyst, functional material and the like is expected.

What is claimed is:

1. A method for producing an arylbis(perfluoroalkylsulfonyl)methane represented by general formula [4]

(Chemical formula 4)

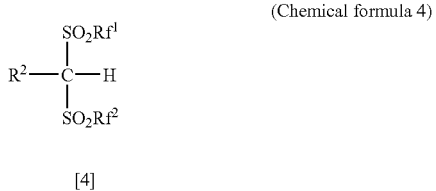

[4]

(wherein $R^1$ shows a substituted or unsubstituted aryl group, $Rf^1$ and $Rf^2$ are independent to each other and show a perfluoroalkyl group), wherein an aryl halomethane is reacted with a perfluoroalkyl sulfinate, an arylmethylperfluoroalkylsulfone produced is reacted with a deprotonation agent comprised of an organic metal or a metallic salt, and a metallic salt of arylmethylperfluoroalkylsulfone obtained is reacted with a perfluoroalkyl sulfonic acid anhydride.

2. The method for producing the arylbis(perfluoroalkylsulfonyl)methane represented by the general formula [4] according to claim 1, wherein the aryl halomethane is reacted with the perfluoroalkyl sulfinate by heating under reflux using a solvent with or without the presence of a catalyst.

3. The method for producing the arylbis(perfluoroalkylsulfonyl)methane represented by the general formula [4] according to claim 2, wherein a tetrabutyl ammonium iodide is used as the catalyst.

4. The method for producing the arylbis(perfluoroalkylsulfonyl)methane represented by the general formula [4] according to claim 2, wherein a propionitrile is used as the solvent.

5. The method for producing the arylbis(perfluoroalkylsulfonyl)methane represented by the general formula [4] according to claim 1, wherein a deprotonation agent comprised of an organic metal or a metallic salt having an equivalent weight of 1.7 to 2.4 is reacted to the arylmethylperfluoroalkylsulfone.

6. The method for producing the arylbis(perfluoroalkylsulfonyl)methane represented by the general formula [4] according to claim 1, wherein the aryl halomethane is a benzyl bromide, a 2-bromomethylnaphthalene, a 1-chloromethylnaphthalene, a 2,4,6-trimethylphenylmethylchloride, a 4-(trifluoromethyl)phenylmethylbromide, a 3,5-bis(trifluoromethyl)phenylmethylbromide, a pentafluorophenylmethylbromide or a 4-(bromomethyl)perfluorobiphenyl.

7. The method for producing the arylbis(perfluoroalkylsulfonyl)methane represented by the general formula [4] according to claim 1, wherein the perfluoroalkyl sulfonate is an alkaline metallic salt of trifluoromethane sulfinic acid.

8. The method for producing the arylbis(perfluoroalkylsulfonyl)methane represented by the general formula [4] according to claim 1, wherein the metallic salt of arylmethylperfluoroalkylsulfone is a lithium salt or a magnesium salt of arylmethylperfluoroalkylsulfone.

9. The method for producing the arylbis(perfluoroalkylsulfonyl)methane represented by the general formula [4] according to claim 1, wherein the arylbis(perfluoroalkylsulfonyl)methane represented by the general formula [4] is an arylbis(trifluoromethylsulfonyl)methane represented by general formula [5]

[5]

(wherein $R^2$ shows a substituted or unsubstituted aryl group).

10. The method for producing the arylbis(perfluoroalkylsulfonyl)methane represented by the general formula [4] according to claim 9, wherein the arylbis(perfluoroalkylsulfonyl)methane represented by the general formula [5] is a pentafluorophenylbis(trifluoromethylsulfonyl)methane represented by formula [2]

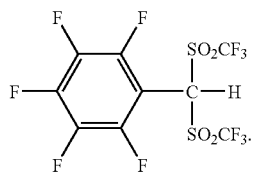
[2]
11. The method for producing the arylbis(perfluoroalkylsulfonyl)methane represented by the general formula [4] according to claim 9, wherein the arylbis(trifluoromethylsulfonyl)methane represented by general formula [5] is a {4-(pentafluorophenyl)-2,3,5,6-tetrafluorophenyl}bis(triflyl)methane represented by formula [3]
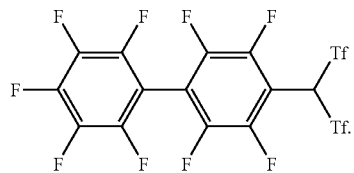
[3]
* * * * *